(12) United States Patent
Andersen et al.

(10) Patent No.: US 11,932,631 B2
(45) Date of Patent: Mar. 19, 2024

(54) PROCESS FOR PREPARING AFICAMTEN

(71) Applicant: Cytokinetics, Inc., South San Francisco, CA (US)

(72) Inventors: Denise Andersen, Montara, CA (US); Matthew Pfeiffer, Salt Lake City, UT (US); Norma Tom, Belmont, CA (US); Bradley P. Morgan, South San Francisco, CA (US)

(73) Assignee: CYTOKINETICS, INC., South San Francisco, CA (US)

( * ) Notice: Subject to any disclaimer, the term of this patent is extended or adjusted under 35 U.S.C. 154(b) by 0 days.

(21) Appl. No.: 17/816,898

(22) Filed: Aug. 2, 2022

(65) Prior Publication Data

US 2023/0045450 A1 Feb. 9, 2023

Related U.S. Application Data

(60) Provisional application No. 63/203,888, filed on Aug. 3, 2021.

(51) Int. Cl.
*C07D 413/12* (2006.01)
*C07C 255/58* (2006.01)

(52) U.S. Cl.
CPC .................. *C07D 413/12* (2013.01)

(58) Field of Classification Search
CPC .... C07D 413/12; C07C 255/58; C07C 313/06
See application file for complete search history.

(56) References Cited

U.S. PATENT DOCUMENTS

| | | |
|---|---|---|
| 10,836,755 B2 | 11/2020 | Chuang et al. |
| 11,472,796 B2 | 10/2022 | Chuang et al. |
| 2006/0173183 A1 | 8/2006 | Powers |
| 2007/0155737 A1 | 7/2007 | Gallagher et al. |
| 2008/0021024 A1 | 1/2008 | Sucholeiki et al. |
| 2008/0176870 A1 | 7/2008 | Nolte et al. |
| 2011/0028463 A1 | 2/2011 | Nozawa et al. |
| 2020/0277262 A1 | 9/2020 | Jones et al. |
| 2022/0315571 A1 | 10/2022 | Tom et al. |

FOREIGN PATENT DOCUMENTS

| | | |
|---|---|---|
| CN | 114835687 A | 8/2022 |
| WO | 2006083454 A1 | 8/2006 |
| WO | 2021011807 A1 | 1/2021 |
| WO | 2022172037 A1 | 8/2022 |
| WO | 2023040830 A1 | 3/2023 |

OTHER PUBLICATIONS

International Search Report and Written Opinion, dated Oct. 28, 2022, for PCT Application No. PCT/US2022/074427, filed on Aug. 2, 2022, 13 pages.
U.S. Appl. No. 17/823,910, filed Aug. 31, 2022, for Chihyuan et al.
CAS SciFinder. (Nov. 30, 2023). "Reactions. Task History. 31-614-CAS-35984908," SciFinder, 4 pages.

*Primary Examiner* — Kamal A Saeed
(74) *Attorney, Agent, or Firm* — MORRISON & FOERSTER LLP

(57) ABSTRACT

Provided herein is a process for the preparation of (R)—N-(5-(5-ethyl-1,2,4-oxadiazol-3-yl)-2,3-dihydro-1H-inden-1-yl)-1-methyl-1H-pyrazole-4-carboxamide, intermediates thereof, and salts of the foregoing.

32 Claims, No Drawings

PROCESS FOR PREPARING AFICAMTEN

CROSS-REFERENCE TO RELATED APPLICATION

This application claims priority to U.S. Provisional Application No. 63/203,888, filed Aug. 3, 2021, the contents of which are hereby incorporated by reference in their entirety for all purposes.

FIELD

Provided herein is a process for the preparation of (R)—N-(5-(5-ethyl-1,2,4-oxadiazol-3-yl)-2,3-dihydro-1H-inden-1-yl)-1-methyl-1H-pyrazole-4-carboxamide, intermediates thereof, and salts of the foregoing.

BACKGROUND

The cardiac sarcomere is composed of a network of contractile and structural proteins that regulate cardiac muscle function. The components of the cardiac sarcomere present targets for the treatment of various cardiac diseases and conditions, for example by increasing contractility or facilitating complete relaxation to modulate systolic and diastolic function, respectively. The force and speed of cardiac muscle contraction is a major determinant of organ function and is modulated by the cyclical interactions of actin and myosin. Regulation of actin and myosin binding is determined by a network of myofilament regulatory proteins and the level of intracellular $Ca^{2+}$. The troponin complex and tropomyosin are thin filament proteins which govern the availability of actin binding sites, and the essential and regulatory light chains, and myosin binding protein C modulate the position and mechanical properties of myosin.

Abnormalities in the cardiac sarcomere have been identified as the driving cause for a variety of cardiac diseases and conditions, such as hypertrophic cardiomyopathy (HCM) and heart failure with preserved ejection fraction (HFpEF). Mutations in the proteins of the sarcomere cause disease by rendering the cardiac muscle either 'hyper' or 'hypo' contractile. Modulators of the cardiac sarcomere can be used to rebalance contractility and stop or reverse the course of disease.

Current agents that target the cardiac sarcomere, such as inotropes (drugs that increase the contractile ability of the heart) are poorly selective for cardiac tissue, which leads to recognized adverse effects that limit their use. These adverse effects include cell damage caused by an increased rate of energy expenditure, exacerbation of relaxation abnormalities, and potential arrhythmogenic side effects that may result from increased cytosolic Ca++ and cyclic AMP concentrations in the inotropically stimulated myocardium. Given the limitations of current agents, new approaches are needed to improve cardiac function in HCM and HFpEF.

U.S. Pat. No. 10,836,755 discloses (R)—N-(5-(5-ethyl-1,2,4-oxadiazol-3-yl)-2,3-dihydro-1H-inden-1-yl)-1-methyl-1H-pyrazole-4-carboxamide, a selective allosteric inhibitor of cardiac myosin that has little to no effect on smooth muscle myosin. Benefits of this compound include a wider therapeutic index, less impact on cardiac relaxation, better pharmacokinetics, and better safety, and therefore it provides a potential treatment for cardiac diseases and conditions.

There is a need for improved methods for preparing such compound with low cost and high overall yield and purity.

BRIEF SUMMARY

In one aspect, provided herein is a method of preparing a compound of Formula (1):

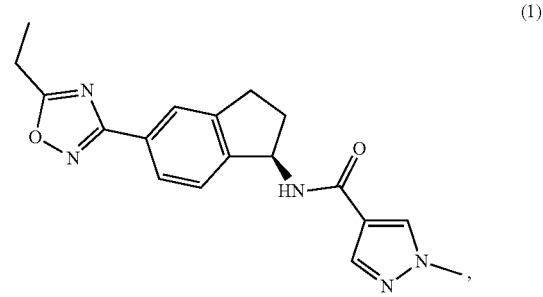 [SMILES: CCc1nc(-c2ccc3c(c2)CC[C@H]3NC(=O)c2cnn(C)c2)no1]

(1)

or a salt thereof, comprising
(i) converting a compound of Formula (7)

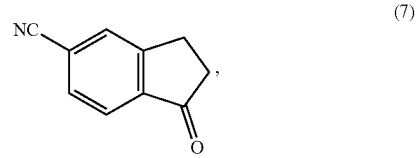 [SMILES: N#Cc1ccc2c(c1)CCC2=O]

(7)

or a salt thereof, to a compound of Formula (6)

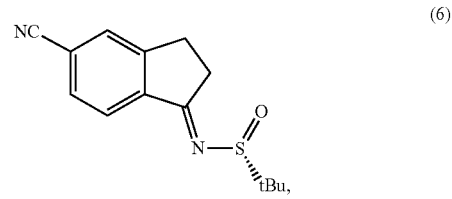 [SMILES: CC(C)(C)[S@@](=O)/N=C1\CCc2cc(C#N)ccc21]

(6)

or salt thereof;
(ii) converting the compound of Formula (6) or salt thereof, to a compound of Formula (5)

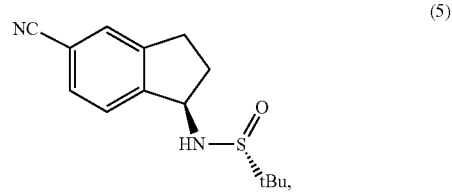 [SMILES: CC(C)(C)[S@@](=O)N[C@@H]1CCc2cc(C#N)ccc21]

(5)

or a salt thereof; and
(iii) converting the compound of Formula (5) or salt thereof to the compound of Formula (1) or a salt thereof. In some embodiments, converting the compound of Formula (7) or salt thereof to the compound of Formula (6) or salt thereof comprises reacting the compound of Formula (7) with (R)-tert-butanesulfinamide. In some embodiments, reacting the compound of Formula (7) with (R)-tert-butanesulfinamide is performed in the presence of a Lewis acid. In some embodiments, reacting the compound of Formula (7) with (R)-tert-butanesulfinamide is performed in the presence of a water scavenger. In some embodiments, reacting the compound of Formula (7) with (R)-tert-butanesulfinamide is performed in the presence of titanium ethoxide. In some embodiments, reacting the compound of Formula (7) with (R)-tert-butanesulfinamide is performed in the presence of toluene at a temperature of between about 75° C. and about 85° C.

In some embodiments, converting the compound of Formula (6) or salt thereof to the compound of Formula (5) or salt thereof comprises reacting the compound of Formula (6) with a reducing agent. In some embodiments, reacting the compound of Formula (6) with a reducing agent is performed in the presence of tetrahydrofuran at a temperature of between about −15° C. and about −5° C. In some embodiments, the reducing agent is sodium borohydride. In some embodiments, the compound of Formula (6) is used without work-up or purification.

In some embodiments, converting the compound of Formula (5) or salt thereof to the compound of Formula (1) or a salt thereof comprises converting the compound of Formula (5) or salt thereof to the compound of Formula (4) or salt thereof.

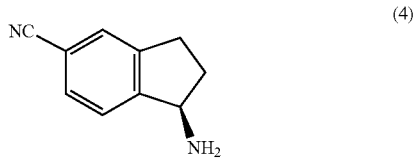 [SMILES: N#Cc1ccc2c(c1)CC[C@H]2N]

(4)

In some embodiments, converting the compound of Formula (5) or salt thereof to the compound of Formula (4) or salt thereof comprises hydrolyzing the sulfinamide of the compound of Formula (5) or salt thereof. In some embodiments, hydrolyzing the sulfinamide of the compound of Formula (5) or salt thereof is performed in the presence of an aqueous acid. In some embodiments, the salt of the compound of Formula (4) is (R)-1-amino-2,3-dihydro-1H-indene-5-carbonitrile hydrochloride. In some embodiments, the salt of the compound of Formula (4) is (R)-1-amino-2,3-dihydro-1H-indene-5-carbonitrile 4-methylbenzenesulfonate. In some embodiments, the method further comprises obtaining the compound of Formula (4) by reacting the salt of the compound of Formula (4) with a base.

In some embodiments, converting the compound of Formula (5) or salt thereof to the compound of Formula (1) further comprises converting the compound of Formula (4) or salt thereof to a compound of Formula (3) or salt thereof.

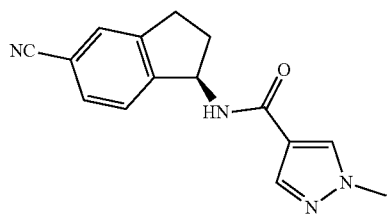

(3)

In some embodiments, converting the compound of Formula (4) or salt thereof to a compound of Formula (3) or salt thereof comprises: (i) reacting 1-methyl-1H-pyrazole-4-carboxylic acid with a carboxylic acid activating agent to form an activated 1-methyl-1H-pyrazole-4-carboxylic acid, and (ii) reacting the activated 1-methyl-1H-pyrazole-4-carboxylic acid with the compound of Formula (4) or a salt thereof, to form the compound of Formula (3) or salt thereof. In some embodiments, carboxylic acid activating agent is oxalyl chloride. In some embodiments, the carboxylic acid activating agent comprises a carbodiimide reagent. In some embodiments, the carboxylic acid activating agent comprises a carbodiimide reagent and hydroxybenzotriazole.

In some embodiments, converting the compound of Formula (5) or salt thereof to the compound of Formula (1) or salt thereof further comprises converting the compound of Formula (3) or salt thereof to a compound of Formula (2) or salt thereof.

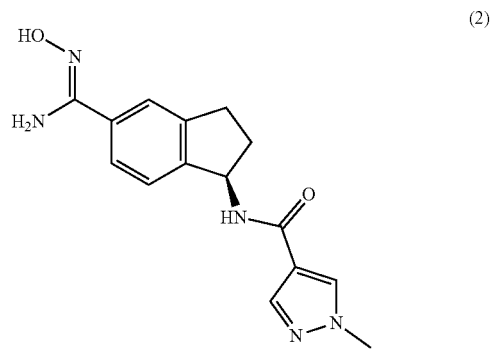 [SMILES: Cn1cc(C(=O)N[C@@H]2CCc3cc(/C(N)=N/O)ccc32)cn1]

(2)

In some embodiments, converting the compound of Formula (3) or salt thereof to a compound of Formula (2) or salt thereof comprises reacting hydroxylamine with the compound of Formula (3) or salt thereof. In some embodiments, reacting the compound of Formula (3) or salt thereof with hydroxylamine is performed at a temperature of 25° C. or lower. In some embodiments, reacting the compound of Formula (3) or salt thereof with hydroxylamine is performed in the presence of N-methylpyrrolidone.

In some embodiments, converting the compound of Formula (5) or salt thereof to the compound of Formula (1) further comprises converting the compound of Formula (2) or salt thereof to the compound of Formula (1) or salt thereof. In some embodiments, converting the compound of Formula (2) or salt thereof to the compound of Formula (1) or salt thereof comprises: (i) reacting propionic acid with a second carboxylic acid activating agent to form an activated propionic acid, and (ii) reacting the activated propionic acid with the compound of Formula (2) or salt thereof. In some embodiments, the second carboxylic acid activating agent is carbonyldiimidazole.

In another aspect, provided is a method of obtaining the compound of Formula (4) or salt thereof by converting a compound of Formula (5):

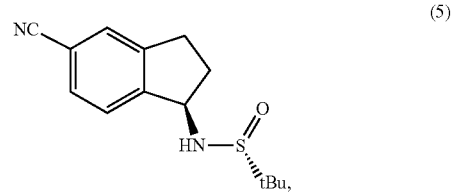 [SMILES: CC(C)(C)[S@@](=O)N[C@@H]1CCc2cc(C#N)ccc21]

(5)

or a salt thereof, to the compound of Formula (4) or salt thereof.

In some embodiments, the method of obtaining the compound of Formula (4) further comprising obtaining the compound of Formula (5) or salt thereof by reacting a reducing agent with a compound of Formula (6):

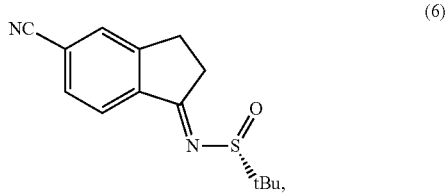 [SMILES: CC(C)(C)[S@@](=O)/N=C1\CCc2cc(C#N)ccc21]

(6)

or a salt thereof, to form the compound of Formula (5) or salt thereof.

In some embodiments, the reducing agent is a borohydride reducing agent.

In some embodiments, the method of obtaining the compound of Formula (4) further comprises obtaining the compound of Formula (6) or salt thereof by reacting (R)-tert-butanesulfinamide with a compound of Formula (7):

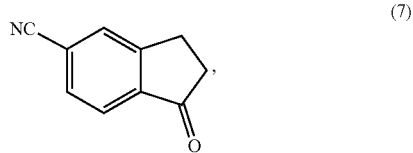 [SMILES: N#Cc1ccc2c(c1)CCC2=O]

(7)

to form the compound of Formula (6) or salt thereof.

DETAILED DESCRIPTION

Definitions

As used herein and unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as used in the specification and the appended claims, the singular forms "a," "an," and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Embodiments also specifically include those compounds, compositions, compositions or methods that are, or that consist of, or that consist essentially of those specified components, elements or steps. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, the term "consisting essentially of" admits for the inclusion of unrecited elements that have no material effect on the functionality of the disclosed compositions, devices, articles of manufacture or methods for its intended purpose as further defined herein. The section headings used herein are for organizational purposes only and are not to be construed as limiting the subject matter described.

"About" as used herein when used in connection with a numeric value or range of values provided to describe a particular property of a compound or composition indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicates that the numeric value or range of values can vary by 10% of the recited value or range of values, while still describing the particular property.

"Protecting group" as used herein, unless otherwise stated or implied by context, refers to a moiety that prevents or substantially reduces the ability of the atom or functional group to which it is linked from participating in unwanted reactions. Typical protecting groups for atoms or functional groups are given in Greene (2014), "Protective groups in organic synthesis, 5$^{th}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is in some embodiments protected as an ester (e.g., acetate, propionate or benzoate). Other protecting groups for hydroxyl avoid its interference with the nucleophilicity of organometallic reagents or other highly base reagents, for which purpose hydroxyl is in some embodiments protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$, wherein at least one of R$^{PR}$ is a nitrogen atom protecting group or both R$^{PR}$ together define a nitrogen atom protecting group.

A protecting group is suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. For example, a suitable protecting group for the basic nitrogen atom of an acyclic or cyclic basic group is an acid-labile carbamate protecting group such as t-butyloxycarbonyl (Boc).

Each compound disclosed herein may be in a salt form. The compound may contain at least one amino group, and accordingly acid addition salts can be formed with this amino group. Exemplary salts include, without limitation, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

A salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a salt can have one or more charged atoms and/or one or more counterions.

"Pharmaceutically acceptable salt" refers to salts which possess toxicity profiles within a range that affords utility in pharmaceutical applications. In some embodiments, a pharmaceutically acceptable salt is selected from those described in P. H. Stahl and C. G. Wermuth, editors, *Handbook of Pharmaceutical Salts: Properties, Selection and Use*, Weinheim/Zürich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

Methods

In one aspect, provided herein is a method of preparing a compound of Formula (1):

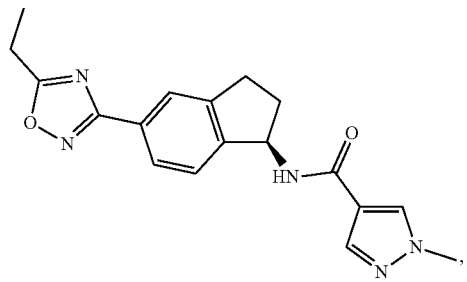

or a salt thereof, comprising (i) converting a compound of Formula (7)

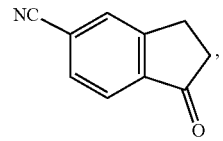

or a salt thereof, to a compound of Formula (6)

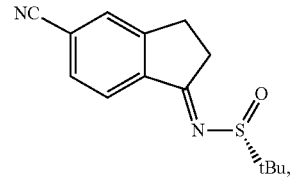

or salt thereof;

(ii) converting the compound of Formula (6) or salt thereof, to a compound of Formula (5)

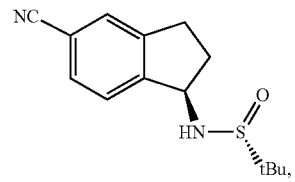

or a salt thereof; and (iii) converting the compound of Formula (5) or salt thereof to the compound of Formula (1) or a salt thereof.

In some embodiments, converting the compound of Formula (5) or salt thereof to the compound of Formula (1) or a salt thereof comprises converting the compound of Formula (5) or salt thereof to the compound of Formula (4) or salt thereof.

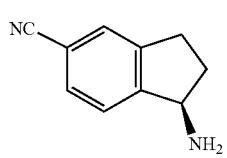

In some embodiments, converting the compound of Formula (5) or salt thereof to the compound of Formula (1) further comprises converting the compound of Formula (4) or salt thereof to a compound of Formula (3) or salt thereof.

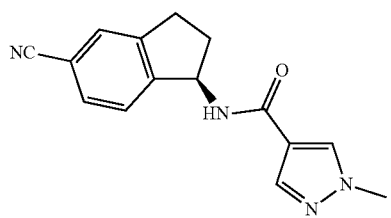
(3)

In some embodiments, converting the compound of Formula (5) or salt thereof to the compound of Formula (1) or salt thereof further comprises converting the compound of Formula (3) or salt thereof to a compound of Formula (2) or salt thereof.

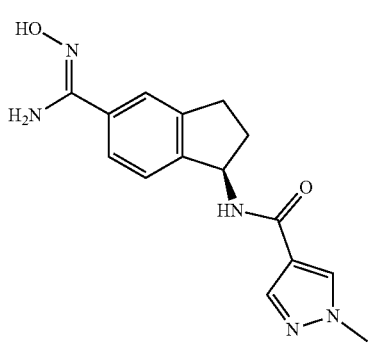
(2)

In some embodiments, converting the compound of Formula (5) or salt thereof to the compound of Formula (1) further comprises converting the compound of Formula (2) or salt thereof to the compound of Formula (1) or salt thereof.

In some embodiments of the foregoing, provided herein is a method of preparing the compound of Formula (1) in accordance with the scheme below:

General Preparation of the Compound of Formula (1)

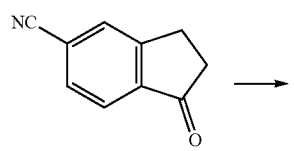
(7)

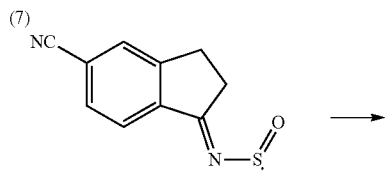
(6)

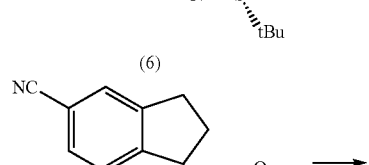
(5)

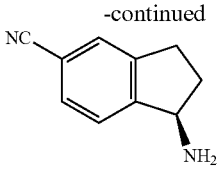
(4)

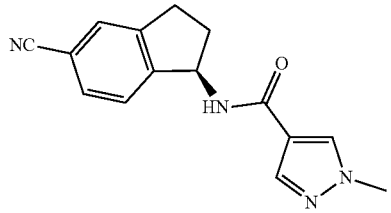
(3)

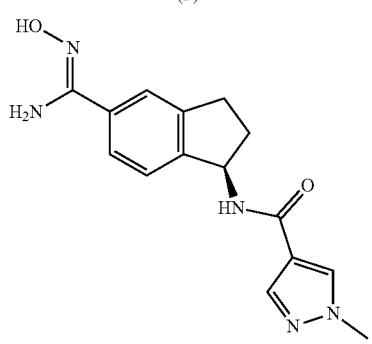
(2)

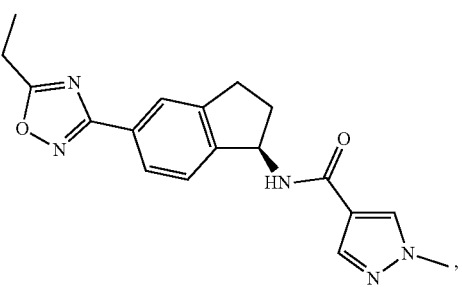
(1)

Preparation of the Compound of Formula (1)

In one aspect, provided herein is a method of preparing a compound of Formula (1):

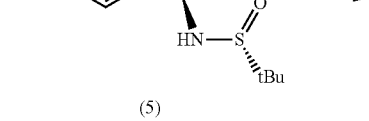
(1)

or a salt thereof, comprising converting a compound of Formula (2):

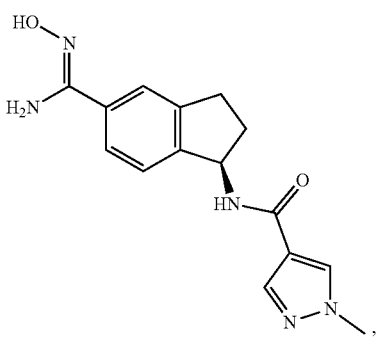

(2)

or a salt thereof, to the compound of Formula (1) or a salt thereof. In some embodiments, provided is a method of preparing a compound of Formula (1) comprising converting a compound of Formula (2) to the compound of Formula (1).

In some embodiments, the method of converting a compound of Formula (2) or a salt thereof to the compound of Formula (1) or a salt thereof comprises reacting the compound of Formula (2) or a salt thereof with propionic acid, an activated propionic acid, or a propionyl equivalent such as propionyl chloride or propionyl bromide. In some embodiments, activated propionic acids include, without limitation, propionic anhydride, 1H-imidazole-1-carboxylic propionic anhydride, propionic acid esters such as methyl propionate, ethyl propionate, propyl propionate, isopropyl propionate, butyl propionate, and tert-butyl propionate.

In some embodiments, the reaction of the compound of Formula (2) or a salt thereof with propionic acid, an activated propionic acid, or a propionyl equivalent is performed in the presence of an organic solvent. In some embodiments, organic solvents include, without limitation, acetonitrile (ACN or MeCN), benzene, chloroform, dichloromethane (DCM), dimethylformamide (DMF), dimethylsulfoxide (DMSO), 1,4-dioxane, N-methylpyrrolidone (NMP), tetrahydrofuran (THF), 2-methyl-tetrahydrofuran (2-MeTHF), toluene, and the like. In some embodiments, the organic solvent is free or substantially free of water. In some embodiments, the organic solvent is any compatible mixture of organic solvents such as those given as embodiments herein. In some embodiments, the organic solvent is a mixture of DMF and toluene. In some embodiments, the organic solvent is DMF. In some embodiments, the organic solvent is 1,4-dioxane. In some embodiments, the organic solvent is acetonitrile. It is understood that each description of the organic solvent may be combined with each description of propionic acid, activated propionic acid, or propionyl equivalent, the same as if each and every combination were specifically and individually listed.

In some embodiments, the reaction of the compound of Formula (2) or a salt thereof with propionic acid, an activated propionic acid, or a propionyl equivalent further comprises a base. In some embodiments, the reaction of the compound of Formula (2) or a salt thereof with propionic acid, an activated propionic acid, or a propionyl equivalent is performed in the presence of a base. In some embodiments, the reaction of the compound of Formula (2) or a salt thereof with propionic acid, an activated propionic acid, or a propionyl equivalent is followed by addition of a base. In some embodiments, the base is an inorganic base. In some embodiments, inorganic bases include, without limitation, potassium carbonate, sodium carbonate, cesium carbonate, potassium bicarbonate, sodium bicarbonate, sodium hydroxide, potassium hydroxide, magnesium hydroxide, lithium hydroxide, and the like. In some embodiments, the base is a carbonate base. In some embodiments, the base is potassium carbonate. In some embodiments, the base is an organic base. In some embodiments, organic bases include, without limitation, N,N-diisopropylethylamine, methylamine, propylamine, trimethylamine, diethylamine, triethylamine, tributylamine, N,N-dimethylethanolamine, tris(hydroxymethyl)aminomethane, ethanolamine, collidine, lutidine, pyridine, picoline, dicyclohexylamine, morpholine, 1,8-diazabicyclo[5.4.0]undec-7-ene (DBU), 1,5-diazabicyclo[4.3.0]non-5-ene (DBN), imidazole, benzimidazole, histidine, guanidine, and the like. In some embodiments, the base is DBU. It is understood that each description of the base may be combined with each description of the organic solvent and each description of the propionic acid, activated propionic acid, or propionyl equivalent, the same as if each and every combination were specifically and individually listed.

In some embodiments, the reaction of the compound of Formula (2) or a salt thereof with propionic acid, an activated propionic acid, or a propionyl equivalent is performed at a temperature of about 153° C., about 150° C., about 140° C., about 130° C., about 120° C., about 111° C., about 110° C., about 100° C., about 90° C., about 82° C., about 80° C., about 70° C., about 60° C., about 50° C., about 40° C., about 30° C., about 20° C., about 10° C., about 0° C., about −10° C., about −20° C., about −30° C., about −40° C., about −50° C., or about −60° C. In some embodiments, the reaction is performed at a temperature of about 130° C., about 120° C., about 110° C., about 100° C., about 90° C., about 80° C., about 70° C., about 60° C., about 50° C., or about 40° C. In some embodiments, the reaction is performed at a temperature of between about 0° C. and about 153° C., between about 0° C. and about 150° C., between about 0° C. and about 100° C., between about 20° C. and about 100° C., between about 20° C. and about 80° C., between about 30° C. and about 70° C., between about 40° C. and about ° C., or between about 45° C. and about 55° C. In some embodiments, the reaction is performed at a temperature of between about 110° C. and about 130° C. In some embodiments, the reaction is performed at a temperature of between about 90° C. and about 110° C. In some embodiments, the reaction is performed at a temperature of between about 50° C. and about 70° C. In some embodiments, the reaction is performed in the presence of DMF and toluene at a temperature of about 120° C., about 110° C., about 100° C., about 90° C., about 80° C., about 70° C., about 60° C., or about 50° C. In some embodiments, the reaction is performed in the presence of DMF and toluene at a temperature of about 120° C., about 110° C., or about 100° C. In some embodiments, the reaction is performed in the presence of DMF and toluene at a temperature of about 120° C. In some embodiments, the reaction is performed in the presence of 1,4-dioxane at a temperature of about 100° C., about 90° C., about 80° C., about 70° C., about 60° C., or about 50° C. In some embodiments, the reaction is performed in the presence of 1,4-dioxane at a temperature of about 100° C. In some embodiments, the reaction is performed in the presence of acetonitrile at a temperature of about 80° C., about 70° C., about 60° C., or about 50° C. In some embodiments, the reaction is performed in the presence of acetonitrile at a temperature of about 70° C. In some embodiments, the reaction is performed in the presence of acetonitrile at a temperature of about 50° C. In some embodiments, the reaction is performed in the presence of acetonitrile at a temperature of between about 40° C. and about 80° C. In some embodiments, the reaction is performed in the presence of acetonitrile at a temperature of between about 50° C. and about 70° C. It is understood that each description of the temperature or range of temperatures may be combined with each description of propionic acid, activated propionic acid, or propionyl equivalent, each description of organic solvent, and/or each description of base, the same as if each and every combination were specifically and individually listed.

In some embodiments, the reaction is performed in the presence of a solvent selected from acetonitrile, DMF, toluene, and 1,4-dioxane, or a mixture of the foregoing; at a temperature of about 100° C. or lower, about 90° C. or lower, about 80° C. or lower, about 70° C. or lower, about 60° C. or lower, about 50° C. or lower, about 40° C. or lower, or about 30° C. or lower; and is followed by addition of a base selected from DBU, DBN, potassium carbonate, and DIEA, with an increase in the temperature by about 5° C., about 10° C., about 20° C., about 30° C., or about 40° C. In some embodiments, the reaction is performed in the presence of acetonitrile at a temperature of about 50° C. or lower, followed by addition of a base such as DBU and an increase in the temperature of about 20° C. or more. In some embodiments, the reaction is performed in the presence of acetonitrile at a temperature of about 50° C. or lower, followed by addition of a base such as DBU and an increase in the temperature of about 20° C. In some embodiments, the reaction is performed in the presence of acetonitrile at a temperature of about 50° C. or lower, followed by addition of a base such as DBU and an increase in the temperature to about 70° C. It is understood that each description of the solvent may be combined with each description of propionic acid, activated propionic acid, or propionyl equivalent, and/or each description of base, the same as if each and every combination were specifically and individually listed.

In another aspect, provided herein is a method of preparing a compound of Formula (1):

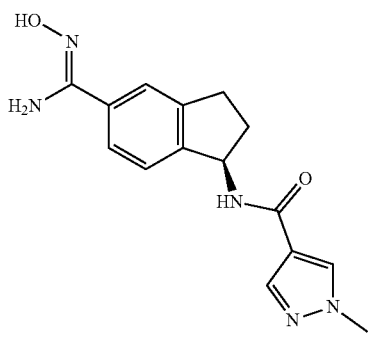

or a salt thereof, comprising:
(i) reacting propionic acid with a first carboxylic acid activating agent to form an activated propionic acid, and
(ii) reacting the activated propionic acid of step (i) with a compound of Formula (2):

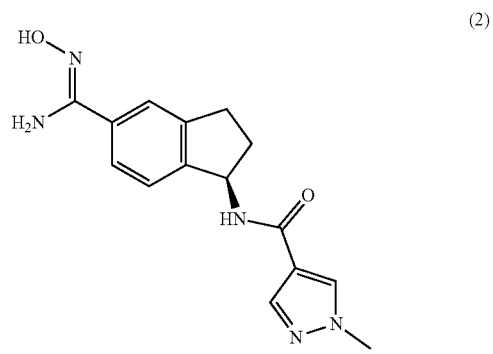 [SMILES: Cn1cc(C(=O)N[C@@H]2CCc3cc(/C(N)=N/O)ccc32)cn1]

or a salt thereof, to form the compound of Formula (1) or a salt thereof. In some embodiments, the method comprises reacting the activated propionic acid of step (i) with a compound of Formula (2) to form the compound of Formula (1).

In some embodiments, carboxylic acid activating agents include acid chlorides such as thionyl chloride, oxalyl chloride, or methanesulfonyl chloride; acid anhydrides such as acetic anhydride; carbodiimides such as N,N'-dicyclohexylcarbodiimide (DCC), 1,3-diisopropylcarbodiimide (DIC), or 1-ethyl-3-(3-dimethylaminopropyl)carbodiimide (EDC, EDAC, or EDCI), optionally in the presence of 1-hydroxy-7-azabenzotriazole (HOAt) or hydroxybenzotriazole (HOBt); or other amide coupling reagents such as hexafluorophosphate azabenzotriazole tetramethyl uronium (HATU), hexafluorophosphate benzotriazole tetramethyl uronium (HBTU), O-(1H-6-chlorobenzotriazole-1-yl)-1,1,3,3-tetramethyluronium hexafluorophosphate (HCTU), (benzotriazol-1-yloxy)tris(dimethylamino)phosphonium hexafluorophosphate (BOP), (7-azabenzotriazol-1-yloxy)tripyrrolidinophosphonium hexafluorophosphate (PyAOP), benzotriazol-1-yloxytripyrrolidinophosphonium hexafluorophosphate (PyBOP), bromotripyrrolidinophosphonium hexafluorophosphate (PyBroP); and carbonyldiimidazole. In some embodiments, the first carboxylic acid activating agent of step (i) (the step of reacting propionic acid with a first carboxylic acid activating agent to form an activated propionic acid) is carbonyldiimidazole.

In some embodiments, step (i) (reacting propionic acid with a first carboxylic acid activating agent to form an activated propionic acid) and step (ii) (reacting the activated propionic acid of step (i) with a compound of Formula (2)) are each performed in an organic solvent. In some embodiments, step (i) and step (ii) are each performed in the same organic solvent. In some embodiments, organic solvents include, without limitation, acetonitrile (ACN or MeCN), benzene, chloroform, dichloromethane (DCM), dimethylformamide (DMF), dimethylsulfoxide (DMSO), 1,4-dioxane, N-methylpyrrolidone (DMP), tetrahydrofuran (THF), 2-methyl-tetrahydrofuran (2-MeTHF), toluene, and the like. In some embodiments, the organic solvent is any compatible mixture of organic solvents such as those given as embodiments herein. In some embodiments, the organic solvent is free or substantially free of water. In some embodiments, the organic solvent comprises water. In some embodiments, the organic solvent for step (i) comprises acetonitrile. In some embodiments, the organic solvent for step (ii) comprises acetonitrile. In some embodiments, the organic solvent for both step (i) and step (ii) comprises acetonitrile. In some embodiments, the organic solvent for step (ii) comprises 1,4-dioxane. In some embodiments, the organic solvent for both step (i) and step (ii) comprises 1,4-dioxane.

In some embodiments, step (ii) (reacting the activated propionic acid of step (i) with a compound of Formula (2)) further comprises a base. In some embodiments, step (ii) is performed in the presence of a base. In some embodiments, step (ii) is followed by addition of a base. In some embodiments, the base is an inorganic base. In some embodiments, inorganic bases include, without limitation, potassium carbonate, sodium carbonate, cesium carbonate, potassium bicarbonate, sodium bicarbonate, sodium hydroxide, potassium hydroxide, magnesium hydroxide, lithium hydroxide, and the like. In some embodiments, the base is a carbonate base. In some embodiments, the base is potassium carbonate. In some embodiments, the base is an organic base. In some embodiments, organic bases include, without limitation, N,N-diisopropylethylamine, methylamine, propylamine, trimethylamine, diethylamine, triethylamine, tributylamine, N,N-dimethylethanolamine, tris(hydroxymethyl)aminomethane, ethanolamine, collidine, lutidine, pyridine, picoline, dicyclohexylamine, morpholine, DBU, DBN, imidazole, benzimidazole, histidine, guanidine, and the like. In some embodiments, the base is DBU. It is understood that each description of the base may be combined with each description of the solvent, the same as if each and every combination were specifically and individually listed.

In some embodiments, step (i) (reacting propionic acid with a first carboxylic acid activating agent to form an activated propionic acid) is performed at a temperature of about 82° C., about 80° C., about 70° C., about 60° C., about 50° C., about 40° C., about 30° C., about 25° C., about ° C., about 10° C., about 0° C., about −10° C., or about −20° C. In some embodiments, step (i) is performed at a temperature of between about 0° C. and about 80° C. In some embodiments, step (i) is performed at a temperature of between about 0° C. and about 50° C. In some embodiments, step (i) is performed at a temperature of between about 10° C. and about 40° C. In some embodiments, step (i) is performed at a temperature of between about 15° C. and about 35° C. In some embodiments, step (i) is performed at a temperature of about 25° C. In some embodiments, step (i) is performed at a temperature of less than about 80° C., less than about 70° C., less than about 60° C., less than about 50° C., less than about 40° C., less than about 35° C., less than about 30° C., or less than about 25° C. In some embodiments, step (i) is performed at a temperature of less than about 35° C., less than about ° C., or less than about 25° C. In some embodiments, step (i) is performed at a temperature of less than about 25° C. In some embodiments, step (ii) (reacting the activated propionic acid of step (i) with a compound of Formula (2)) is performed at a temperature of about 82° C., about 80° C., about ° C., about 60° C., about 50° C., about 40° C., about 30° C., about 25° C., about 20° C., about 10° C., about 0° C., about −10° C., or about −20° C. In some embodiments, step (ii) is performed at a temperature of about 50° C. In some embodiments, step (ii) is performed at a temperature of between about 0° C. and about 80° C. In some embodiments, step (ii) is performed at a temperature of between about 30° C. and about 80° C. In some embodiments, step (ii) is performed at a temperature of between about 45° C. and about 75° C. In some embodiments, step (ii) is performed at a temperature of between about 50° C. and about 70° C. In some embodiments, step (ii) is performed at a temperature of between about 45° C. and about 55° C. In some embodiments, the reaction is performed in the presence of acetonitrile at a temperature of about 50° C. or lower, followed by addition of a base and an increase in the temperature to about 70° C. or higher. It is understood that each description of the temperature may be combined with each description of the base and/or the organic solvent the same as if each and every combination were specifically and individually listed. For example, in some embodiments, step (i) is performed in acetonitrile at a temperature of about 25° C. or lower, step (ii) is performed in acetonitrile at a temperature of about ° C., followed by the addition of DBU and an increase in the temperature to about 70° C. It is understood that each description of the temperature or range of temperatures may be combined with each description of carboxylic activating agent, each description of organic solvent, and/or each description of base, the same as if each and every combination were specifically and individually listed.

In some embodiments, the step (ii) (reacting the activated propionic acid of step (i) with a compound of Formula (2)) is followed by addition of water to the reaction mixture. In some embodiments, the diluted reaction mixture is polish filtered, and the filtrate is concentrated to a slurry. In some embodiments, the diluted reaction mixture is polish filtered, and the filtrate is concentrated to a slurry at a temperature of between about 10° C. and about 50° C. In some embodiments, the slurry is further diluted with water to form a mixture. In some embodiments, the slurry is heated to a temperature of between 70° C. and about 80° C. before diluting with water to form a mixture, while maintaining a temperature of at least about 70° C. of the mixture. In some embodiments, the mixture is filtered to provide the compound of Formula (1) as a solid. In some embodiments, the mixture is cooled to a temperature of between about 15° C. and about 25° C. prior to filtration of the mixture to provide the compound of Formula (1) as a solid. In some embodiments, the compound of Formula (1) is isolated as a wet cake solid. In some embodiments, the wet cake solid of Formula (1) is washed with water and dried under vacuum to form a dry solid. In some embodiments, the dry solid of Formula (1) is de-lumped.

It is to be understood that each description of the conditions for step (i) (reacting propionic acid with a first carboxylic acid activating agent to form an activated propionic acid) and step (ii) (reacting the activated propionic acid of step (i) with a compound of Formula (2)) may be combined, the same as if each and every combination were specifically and individually listed. For example, in some embodiments step (i) comprises reacting propionic acid with carbonyldiimidazole in acetonitrile to prepare the activated propionic acid, and step (ii) comprises reacting the activated propionic acid with a compound of Formula (2), followed by reacting with DBU. For example, in some embodiments step (i) comprises reacting propionic acid with carbonyldiimidazole in acetonitrile at a temperature of 25° C. or lower to prepare the activated propionic acid, and step (ii) comprises reacting the activated propionic acid with a compound of Formula (2) in acetonitrile at a temperature of about 50±5° C., followed by reacting with DBU in acetonitrile at a temperature of about 70±5° C. For example, in some embodiments step (i) comprises reacting propionic acid with carbonyldiimidazole in acetonitrile at a temperature of 25° C. or lower to prepare the activated propionic acid, and step (ii) comprises reacting the activated propionic acid with a compound of Formula (2) in acetonitrile at a temperature of about 50±5° C., followed by reacting with DBU in acetonitrile at a temperature of about 70±5° C., followed by addition of water. For example, in some embodiments step (i) comprises reacting propionic acid with carbonyldiimidazole in acetonitrile at a temperature of 25° C. or lower to prepare the activated propionic acid, and step (ii) comprises reacting the activated propionic acid with a compound of Formula (2) in acetonitrile at a temperature of about 50±5° C., followed by reacting with DBU in acetonitrile at a temperature of about 70±5° C., followed by addition of water, polish filtration, concentration to a slurry at a temperature of between about 10° C. and about 50° C., heating to a temperature of between 70° C. and about 80° C. before diluting with water to form a mixture, cooling to a temperature of between about 15° C. and about 25° C., and filtering the mixture to provide the compound of Formula (1) as a solid.

Preparation of the Compound of Formula (2)

In some embodiments, the compound of Formula (2) or a salt thereof is prepared by converting compound of Formula (3):

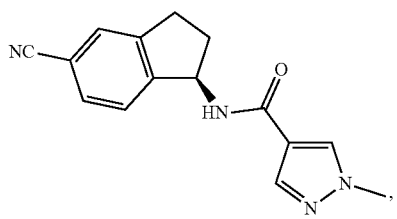

(3)

or a salt thereof, to the compound of Formula (2) or a salt thereof. In some embodiments, the method comprises converting the compound of Formula (2) to the compound of Formula (3). In some embodiments, the method comprises reacting hydroxylamine with the compound of Formula (3) or a salt thereof. In some embodiments, hydroxylamine is provided as aqueous hydroxylamine. In some embodiments, the reaction of hydroxylamine with the compound of Formula (3) is performed in an organic solvent. In some embodiments, organic solvents include, without limitation, acetonitrile, dimethylformamide, dimethylsulfoxide, 1,4-dioxane, N-methylpyrrolidone, tetrahydrofuran, 2-methyl-tetrahydrofuran, methanol, ethanol, isopropanol, and the like. In some embodiments, the organic solvent is any compatible mixture of organic solvents such as those given as examples herein. In some embodiments, the organic solvent comprises water. In some embodiments, the organic solvent comprises ethanol. In some embodiments, the organic solvent comprises NMP.

In some embodiments, the reaction of hydroxylamine with the compound of Formula (3) is performed at a temperature of about 80° C., about 70° C., about 60° C., about 58° C., about 50° C., about 40° C., about 30° C., about 20° C., about 10° C., about 0° C., about −10° C., or about −20° C. In some embodiments, the reaction is performed at a temperature of about 50° C., about 40° C., about 30° C., about 25° C., about 20° C., about 10° C., about 0° C., about −10° C., or about −20° C. In some embodiments, the reaction is performed at a temperature of about 50° C. or lower, about 40° C. or lower, about 30° C. or lower, about 25° C. or lower, about 20° C. or lower, about 10° C. or lower, or about 0° C. or lower. In some embodiments, the reaction is performed at a temperature of between about −20° C. and about 50° C. In some embodiments, the reaction is performed at a temperature of between about −10° C. and 50° C. In some embodiments, the reaction is performed at a temperature of between about 0° C. and about 50° C. In some embodiments, the reaction is performed at a tempera-ture of between about 0° C. and about 40° C. In some embodiments, the reaction is performed at a temperature of between about 0° C. and about 30° C. In some embodiments, the reaction is performed at a temperature of between about 5° C. and about 25° C. In some embodiments, the reaction is performed at a temperature of between about 10° C. and about 25° C. It is understood that each description of the temperature or range of temperatures may be combined with each description of organic solvent, the same as if each and every combination were specifically and individually listed. For example, in some embodiments the method comprises reacting the compound of Formula (3) with aqueous hydroxylamine in NMP, at a temperature of about 10° C. or lower, followed by warming to a temperature of between about 15° C. and about 25° C. For example, in some embodiments the method comprises reacting the compound of Formula (3) with aqueous hydroxylamine in NMP, at room temperature or a temperature of about 25° C.

In some embodiments, after completion of the reaction of hydroxylamine with the compound of Formula (3), the compound of Formula (2) is precipitated by the addition of a cosolvent. In some embodiments, the cosolvent is water. In some embodiments, after completion of the reaction of hydroxylamine with the compound of Formula (3), the compound of Formula (2) is precipitated by the addition of an organic cosolvent. In some embodiments, the cosolvent is an organic acetate. In some embodiments, the cosolvent is ethyl acetate (EtOAc), isopropyl acetate (IPAc), or tert-butyl acetate. In some embodiments, the cosolvent is isopropyl acetate In some embodiments, addition of the cosolvent is performed at a temperature of at least about 30° C., at least about 40° C., at least about 50° C., or at least about 60° C. In some embodiments, addition of the cosolvent is performed at a temperature of between about 50° C. and about 80° C. In some embodiments, addition of the cosolvent is performed at a temperature of between about 50° C. and about 75° C. In some embodiments, addition of the cosolvent is performed at a temperature of about 65° C. In some embodiments, the precipitated compound of Formula (2) is isolated by vacuum filtration as a wet cake. In some embodiments, the compound of Formula (2) is dried under vacuum. It is understood that each description of the precipitation step may be combined with each description of the reaction conditions, the same as if each and every combination were specifically and individually listed. For example, in some embodiments the method comprises reacting the compound of Formula (3) with aqueous hydroxylamine in NMP, at a temperature of about 10° C. or lower, followed by warming to a temperature of between about 15° C. and about 25° C., followed by heating to a temperature of between about 60° C. and 70° C. and adding IPAc. For example, in some embodiments the method comprises reacting the compound of Formula (3) with aqueous hydroxylamine in NMP at room temperature or a temperature of about 25° C., followed by addition of water at room temperature or a temperature of about 25° C.

Preparation of the Compound of Formula (3)

In some embodiments, the compound of Formula (3) or a or a salt thereof is prepared by (iii) reacting 1-methyl-1H-pyrazole-4-carboxylic acid with a second carboxylic acid activating agent to form an activated 1-methyl-1H-pyrazole-4-carboxylic acid, and (iv) reacting the activated 1-methyl-1H-pyrazole-4-carboxylic acid of step (iii) with a compound of Formula (4):

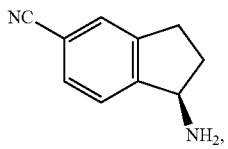
(4)

or a salt thereof, to form the compound of Formula (3) or a salt thereof. In some embodiments, step (iv) comprises reacting the activated 1-methyl-1H-pyrazole-4-carboxylic acid of step (iii) with a compound of Formula (4) to form the compound of Formula (3).

In some embodiments, carboxylic acid activating agents include acid chlorides such as thionyl chloride, oxalyl chloride, or methanesulfonyl chloride; acid anhydrides such as acetic anhydride; carbodiimides such as DCC, DIC, or EDC, optionally in the presence of HOAt or HOBt; or other amide coupling reagents such as HATU, HBTU, HCTU, BOP, PyAOP, PyBOP, PyBroP; and carbonyldiimidazole. In some embodiments, the second carboxylic acid activating agent of step (iii) (reacting 1-methyl-1H-pyrazole-4-carboxylic acid with a second carboxylic acid activating agent to form an activated 1-methyl-1H-pyrazole-4-carboxylic acid) is oxalyl chloride. In some embodiments, the second carboxylic acid activating agent of step (iii) comprises a carbodiimide reagent. In some embodiments, the carbodiimide reagent comprises EDC. In some embodiments, step (iii) is performed in the presence of a carbodiimide reagent and HOAt or HOBt.

In some embodiments, step (iii) (reacting 1-methyl-1H-pyrazole-4-carboxylic acid with a second carboxylic acid activating agent to form an activated 1-methyl-1H-pyrazole-4-carboxylic acid) further comprises a base. In some embodiments, the base is an inorganic base. In some embodiments, inorganic bases include, without limitation, potassium carbonate, sodium carbonate, cesium carbonate, potassium bicarbonate, sodium bicarbonate, sodium hydroxide, potassium hydroxide, magnesium hydroxide, lithium hydroxide, and the like. In some embodiments, the base is an organic base. In some embodiments, organic bases include, without limitation, N,N-diisopropylethylamine (DIEA or DIPEA), methylamine, propylamine, trimethylamine, diethylamine, triethylamine, tributylamine, N,N-dimethylethanolamine, tris(hydroxymethyl)aminomethane, ethanolamine, collidine, lutidine, pyridine, picoline, dicyclohexylamine, morpholine, DBU, DBN, imidazole, benzimidazole, histidine, guanidine, and the like. In some embodiments, the base is an amine base. In some embodiments, the base is selected from N,N-diisopropylethylamine, methylamine, propylamine, trimethylamine, diethylamine, triethylamine, and tributylamine. In some embodiments, the base is diisopropylethylamine. It is understood that each description of the base may be combined with each description of the carboxylic activating agent, the same as if each and every combination were specifically and individually listed. For example, in some embodiments, the reaction is performed in the presence of EDC, HOBt, and DIEA. In other embodiments, reaction is performed in the presence of EDC, HOAt, and DIEA.

In some embodiments, step (iii) (reacting 1-methyl-1H-pyrazole-4-carboxylic acid with a second carboxylic acid activating agent to form an activated 1-methyl-1H-pyrazole-4-carboxylic acid) is performed at a temperature of about 80° C., about 70° C., about 60° C., about 50° C., about 40° C., about 30° C., about 20° C., or about 10° C. In some embodiments, step (iii) is performed at a temperature of below about 80° C. In some embodiments, step (iii) is performed at a temperature of below about 61° C. In some embodiments, step (iii) is performed at a temperature of below about 55° C. In some embodiments, step (iii) is performed at a temperature of below about 50° C. In some embodiments, step (iii) is performed at a temperature of below about 40° C. In some embodiments, step (iii) is performed at a temperature of below about 35° C. In some embodiments, step (iii) is performed at a temperature of between about 0° C. and about 80° C. In some embodiments, step (iii) is performed at a temperature of between about 0° C. and about 60° C. In some embodiments, step (iii) is performed at a temperature of between about 10° C. and about 40° C. In some embodiments, step (iii) is performed at a temperature of between about 20° C. and about 40° C. In some embodiments, step (iii) is performed at a temperature of between about 20° C. and about 35° C. In some embodiments, step (iii) is performed at a temperature of between about 25° C. and about 35° C. It is understood that each description of the temperature or range of temperatures may be combined with each description of the carboxylic activating agent and/or each description of the base, the same as if each and every combination were specifically and individually listed.

In some embodiments, step (iii) (reacting 1-methyl-1H-pyrazole-4-carboxylic acid with a second carboxylic acid activating agent to form an activated 1-methyl-1H-pyrazole-4-carboxylic acid) is performed in an organic solvent as described herein. In some embodiments, the solvent comprises DMF. In some embodiments, the solvent comprises 2-MeTHF. In some embodiments, the organic solvent further comprises water. In some embodiments, the solvent comprises a mixture of solvents as described herein. In some embodiments, the solvent comprises a mixture of DMF and 2-MeTHF. It is understood that solvent may be combined with each description of the carboxylic activating agent, each description of the base, and/or each description of the temperature or range of temperatures, the same as if each and every combination were specifically and individually listed. For example, in some embodiments, step (iii) is performed in the presence of EDC, HOBt, DIEA, and DMF at a temperature of between about 40° C. and about 20° C. In other embodiments, step (iii) is performed in the presence of EDC, HOAt, DIEA, and DMF at a temperature of between about 40° C. and about 20° C. In other embodiments, step (iii) is performed in the presence of oxalyl chloride and DMF at a temperature of between about 40° C. and about 20° C. In other embodiments, step (iii) is performed in the presence of oxalyl chloride and DMF at a temperature of below about 35° C. In other embodiments, the reaction is performed in the presence of oxalyl chloride, 2-MeTHF, and DMF at a temperature of between about 20° C. and about 40° C., between about 20° C. and about 35° C., or between about 25° C. and about 35° C. In other embodiments, the reaction is performed in the presence of oxalyl chloride, 2-MeTHF, and DMF at a temperature of below about 35° C.

In some embodiments, the crude product of step (iii) (reacting 1-methyl-1H-pyrazole-4-carboxylic acid with a second carboxylic acid activating agent to form an activated 1-methyl-1H-pyrazole-4-carboxylic acid) is used without work-up. In some embodiments, the crude product of step (iii) is used without purification.

In some embodiments, step (iv) (reacting the activated 1-methyl-1H-pyrazole-4-carboxylic acid of step (iii) with a compound of Formula (4)) is performed in the presence of a base. In some embodiments, the base is an inorganic base. In some embodiments, inorganic bases include, without limitation, potassium carbonate, sodium carbonate, cesium carbonate, potassium bicarbonate, sodium bicarbonate, sodium hydroxide, potassium hydroxide, magnesium hydroxide, lithium hydroxide, sodium tert-butoxide, potassium carbonate, sodium bis(trimethylsilyl)amide and the like. In some embodiments, the base is a hydroxide base such as sodium hydroxide, potassium hydroxide, magnesium hydroxide, lithium hydroxide. In some embodiments, the base is sodium hydroxide. In some embodiments, the base is an organic base. In some embodiments, organic bases include, without limitation, N,N-Diisopropylethylamine, methylamine, propylamine, trimethylamine, diethylamine, triethylamine, pyridine, or morpholine. In some embodiments, the base is aqueous. In some embodiments, the base is aqueous sodium hydroxide.

In some embodiments, step (iv) (reacting the activated 1-methyl-1H-pyrazole-4-carboxylic acid of step (iii) with a compound of Formula (4)) is performed in an organic solvent as described herein. In some embodiments, the solvent comprises DMF. In some embodiments, the solvent comprises 2-MeTHF. In some embodiments, the organic solvent further comprises water. In some embodiments, the solvent comprises a mixture of solvents as described herein. In some embodiments, the solvent comprises a mixture of DMF and 2-MeTHF. It is understood that each description of the organic solvent of step (iv) may be combined with each description of step (iii) (reacting 1-methyl-1H-pyrazole-4-carboxylic acid with a second carboxylic acid activating agent to form an activated 1-methyl-1H-pyrazole-4-carboxylic acid), each description of the base of step (iv), and/or each description of the temperature or range of temperatures of step (iv), the same as if each and every combination were specifically and individually listed. For example, in some embodiments step (iii) comprises reacting 1-methyl-1H-pyrazole-4-carboxylic acid with oxalyl chloride to form an activated 1-methyl-1H-pyrazole-4-carboxylic acid, and step (iv) comprises reacting the activated 1-methyl-1H-pyrazole-4-carboxylic acid of step (iii) with a compound of Formula (4)) in the presence of NaOH. For example, in some embodiments step (iii) comprises reacting 1-methyl-1H-pyrazole-4-carboxylic acid with oxalyl chloride in DMF and 2-MeTHF to form an activated 1-methyl-1H-pyrazole-4-carboxylic acid, and step (iv) comprises reacting the activated 1-methyl-1H-pyrazole-4-carboxylic acid of step (iii) with a compound of Formula (4)) in the presence of aqueous NaOH. For example, in some embodiments step (iii) comprises reacting 1-methyl-1H-pyrazole-4-carboxylic acid with oxalyl chloride in DMF and 2-MeTHF at a temperature of below about 35° C. to form an activated 1-methyl-1H-pyrazole-4-carboxylic acid, and step (iv) comprises reacting the activated 1-methyl-1H-pyrazole-4-carboxylic acid of step (iii) with a compound of Formula (4)) in the presence of aqueous NaOH at a temperature of below about 30° C. For example, in some embodiments step (iii) and step (iv) comprise reacting 1-methyl-1H-pyrazole-4-carboxylic acid with a compound of Formula (4) in the presence of HOBt, EDC, and DIEA. For example, in some embodiments step (iii) and step (iv) comprise reacting 1-methyl-1H-pyrazole-4-carboxylic acid with a compound of Formula (4) in the presence of HOBt, EDC, and DIEA in DMF.

In some embodiments, the compound of Formula (3) is isolated by filtration to provide a wet cake solid. In some embodiments, the wet cake solid is rinsed with a solvent such as 2-MeTHF or water. In some embodiments, the compound of Formula (3) is dried under vacuum.

Scheme 1 illustrates a scheme of synthesizing the compound of Formula (1).

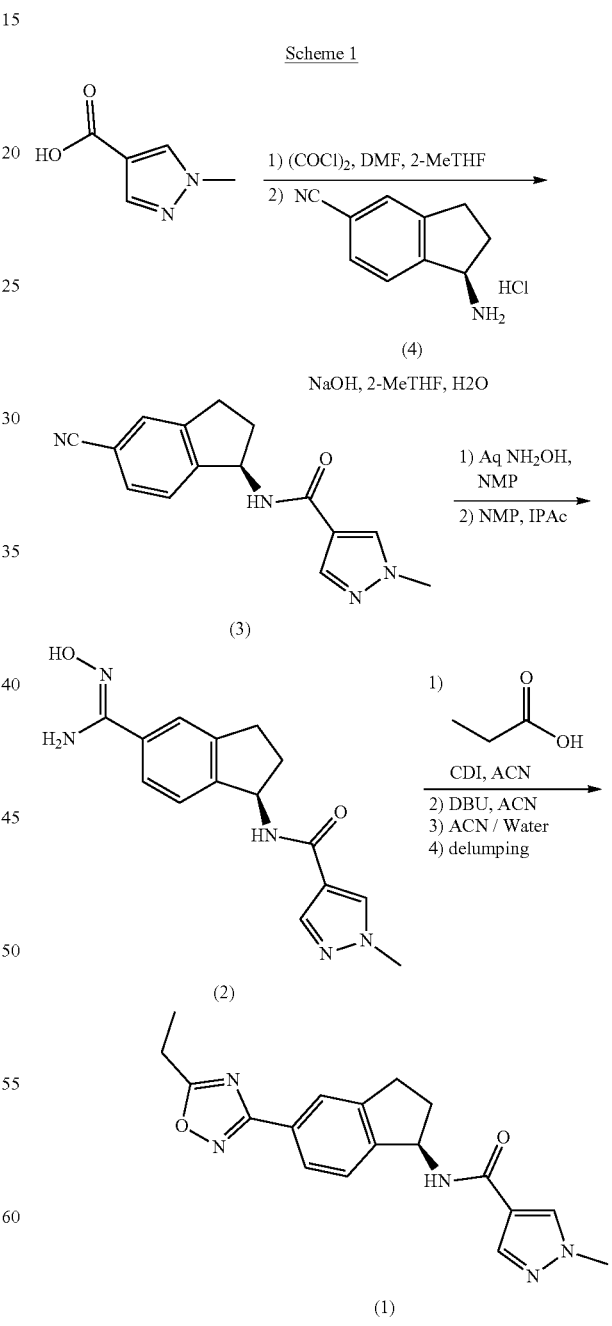

Scheme 2 illustrates an alternative scheme of synthesizing the compound of Formula (2).

Scheme 2

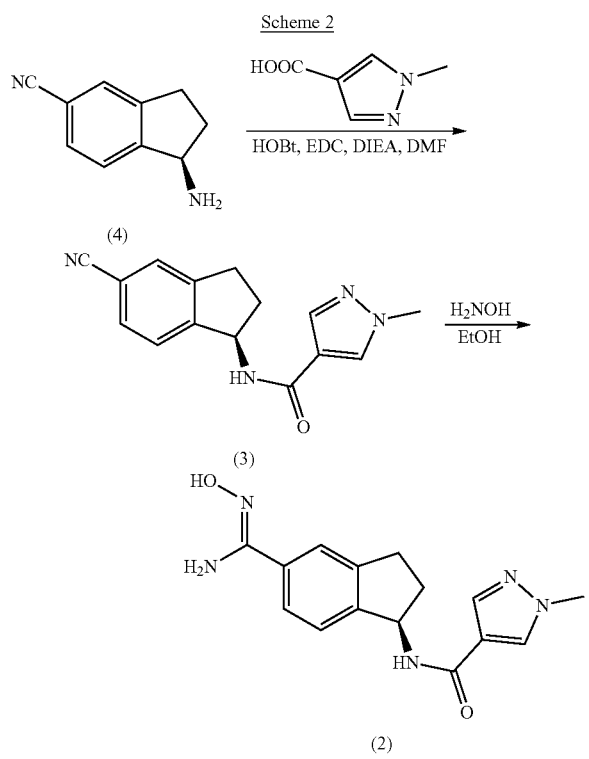

Preparation of a Polymorph of the Compound of Formula (1)

In some embodiments of the foregoing, the method of preparing a compound of Formula (1) further comprises preparing a polymorph of the compound of Formula (1). Methods of preparing polymorphs of the compound of Formula (1) are disclosed in WO2021/011807, the contents of which are incorporated by reference herein in their entirety.

In some embodiments, the polymorph of the compound of Formula (1) is polymorphic Form I. In some embodiments, the polymorphic form is characterized by having an XRPD pattern comprising peaks at angles 2-theta of 3.7±0.2, 11.2±0.2, 12.9±0.2, 14.4±0.2, and 22.4±0.2 degrees. In some embodiments, the polymorph of the compound of Formula (1) is characterized by having an XRPD pattern comprising peaks at angles 2-theta of 3.7±0.2, 11.2±0.2, 12.9±0.2, 13.5±0.2, 14.4±0.2, 18.6±0.2, 22.4±0.2, 24.7±0.2, 25.0±0.2, and 26.1±0.2 degrees.

In some embodiments, the polymorph of the compound of Formula (1) is polymorphic Form II. In some embodiments, the polymorphic form is characterized by having an XRPD pattern comprising peaks at angles 2-theta of 3.7±0.2, 9.8±0.2, 11.1±0.2, 12.8±0.2, and 20.4±0.2 degrees. In some embodiments, the polymorph of the compound of Formula (1) is characterized by having an XRPD pattern comprising peaks at angles 2-theta of 3.7±0.2, 9.8±0.2, 11.1±0.2, 12.8±0.2, 14.7±0.2, 16.1±0.2, 18.5±0.2, 20.4±0.2, 22.3±0.2, and 23.3±0.2 degrees.

In some embodiments, the polymorph of the compound of Formula (1) is polymorphic Form III. In some embodiments, the polymorphic form is characterized as having a XRPD pattern comprising peaks at angles 2-theta of 9.6±0.2, 10.9±0.2, 15.8±0.2, and 18.1±0.2 degrees.

In some embodiments, the polymorph of the compound of Formula (1) is polymorphic Form IV. In some embodiments, the polymorphic form is characterized as having an XRPD pattern comprising peaks at angles 2-theta of 11.1±0.2, 12.8±0.2, 13.5±0.2, 22.8±0.2, and 24.4±0.2 degrees. In some embodiments, the polymorph of the compound of Formula (1) is characterized as having an XRPD pattern comprising peaks at angles 2-theta of 3.7±0.2, 11.1±0.2, 12.8±0.2, 13.5±0.2, 21.9±0.2, 22.8±0.2, 23.1±0.2, 23.5±0.2, 24.4±0.2, and 24.8±0.2 degrees.

In some embodiments, the polymorph of the compound of Formula (1) is polymorphic Form V. In some embodiments, the polymorphic form is characterized by having an XRPD pattern comprising peaks at angles 2-theta of 11.5±0.2, 16.3±0.2, 20.0±0.2, 21.2±0.2, and 24.7±0.2 degrees. In some embodiments, the polymorph of the compound of Formula (1) is characterized by having an XRPD pattern comprising peaks at angles 2-theta of 11.5±0.2, 16.3±0.2, 19.1±0.2, 20.0±0.2, 21.2±0.2, 24.0±0.2, 24.7±0.2, 25.6±0.2, and 26.7±0.2 degrees. In some embodiments, the polymorph of the compound of Formula (1) is characterized by having an XRPD pattern comprising peaks at angles 2-theta of 5.7±0.2, 8.3±0.2, 11.5±0.2, 16.3±0.2, 17.2±0.2, 19.1±0.2, 20.0±0.2, 20.7±0.2, 21.2±0.2, 23.3±0.2, 24.0±0.2, 24.7±0.2, 25.6±0.2, 26.7±0.2, 28.1±0.2, 29.2±0.2, 29.7±0.2, 29.9±0.2, and 31.1±0.2 degrees.

In some embodiments, the polymorph of the compound of Formula (1) is polymorphic Form VI. In some embodiments, the polymorphic form is characterized by having an XRPD pattern comprising peaks at angles 2-theta of 10.6±0.2, 12.1±0.2, 15.0±0.2, 16.1±0.2, and 17.8±0.2 degrees. In some embodiments, the polymorph of the compound of Formula (1) is characterized by having an XRPD pattern comprising peaks at angles 2-theta of 5.4±0.2, 5.9±0.2, 8.1±0.2, 9.6±0.2, 10.6±0.2, 12.1±0.2, 14.0±0.2, 15.0±0.2, 16.1±0.2, and 17.8±0.2 degrees.

Preparation of the Compound of Formula (4)

In another aspect, provided herein is a method of preparing a compound of Formula (4):

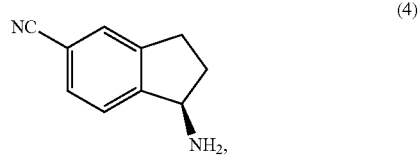 [SMILES: N#Cc1ccc2c(c1)CC[C@H]2N]

or a salt thereof, by converting a compound of Formula (5):

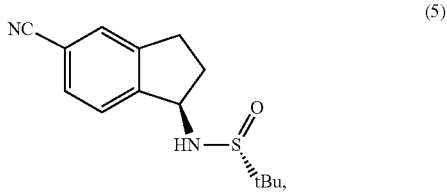 [SMILES: CC(C)(C)[S@@](=O)N[C@@H]1CCc2cc(C#N)ccc21]

or a salt thereof, to the compound of Formula (4), or a salt thereof. In some embodiments, the method comprises converting a compound of Formula (5) to the compound of Formula (4) or a salt thereof. In some embodiments, the method of preparing the compound of Formula (4) or a salt thereof comprises hydrolyzing the sulfinamide of the compound of Formula (5) or a salt thereof.

In some embodiments, the sulfinamide of the compound of Formula (5) is hydrolyzed in the presence of an aqueous acid. In some embodiments, the aqueous acid of step is an inorganic acid. In some embodiments, inorganic acids include, without limitation, hydrochloric acid, hydrobromic acid, sulfuric acid, nitric acid, phosphoric acid, and the like. In some embodiments, the aqueous acid is an organic acid. In some embodiments, organic acids include acetic acid, propionic acid, ascorbic acid, citric acid, trifluoroacetic acid, toluenesulfonic acid, and the like. In some embodiments, the aqueous acid is any compatible mixture of acids such as those given as embodiments herein. In some embodiments, the aqueous acid is hydrochloric acid.

In some embodiments, the sulfinamide of the compound of Formula (5) is hydrolyzed in the presence of a base. In some embodiments, the sulfinamide is hydrolyzed in the presence of an aqueous base. In some embodiments, the base is an inorganic base. In some embodiments, inorganic bases include, without limitation, potassium carbonate, sodium carbonate, cesium carbonate, potassium bicarbonate, sodium bicarbonate, sodium hydroxide, potassium hydroxide, magnesium hydroxide, lithium hydroxide, and the like. In some embodiments, the base is an organic base. In some embodiments, organic bases include, without limitation, N,N-diisopropylethylamine, methylamine, propylamine, trimethylamine, diethylamine, triethylamine, tributylamine, N,N-dimethylethanolamine, tris(hydroxymethyl)aminomethane, ethanolamine, collidine, lutidine, pyridine, picoline, dicyclohexylamine, morpholine, DBU, DBN, imidazole, benzimidazole, histidine, guanidine, and the like.

In some embodiments, the hydrolysis of the sulfinamide is performed in an organic solvent. In some embodiments, organic solvents include, without limitation, acetonitrile, dimethylformamide, dimethylsulfoxide, 1,4-dioxane, N-methylpyrrolidone, tetrahydrofuran, 2-methyl-tetrahydrofuran, methanol, ethanol, isopropanol, ethyl acetate, isopropyl acetate, tert-butyl acetate, and the like. In some embodiments, the solvent is isopropyl acetate. In some embodiments, the organic solvent is any compatible mixture of organic solvents such as those given as embodiments herein. In some embodiments, the organic solvent comprises water. It is to be understood that each description of the acid or base may be combined with each description of the organic solvent, the same as if each and every combination were specifically and individually listed. For example, in some embodiments, the hydrolysis of the sulfinamide is performed in the presence of aqueous HCl. For example, in some embodiments, the hydrolysis of the sulfinamide is performed in the presence of IPAc. For example, in some embodiments, the hydrolysis of the sulfinamide is performed in the presence of aqueous HCl and IPAc.

In some embodiments, the compound of Formula (4) is collected by filtration. In some embodiments, filtration provides the compound of Formula (4) as a wet cake. In some embodiments, the wet cake solid compound of Formula (4) is washed with IPAc. In some embodiments, the compound of Formula (4) is dried under vacuum.

Preparation of the Compound of Formula (5)

In some embodiments, the compound of Formula (5) or a salt thereof is prepared by reacting a reducing agent with a compound of Formula (6):

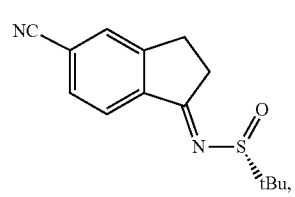

or a salt thereof, to form the compound of Formula (5) or a salt thereof. In some embodiments, the method comprises reacting a reducing agent with the compound of Formula (6) to form the compound of Formula (5). In some embodiments, reducing agents include, without limitation, hydrogen in the presence of a catalyst such as a palladium catalyst, lithium aluminum hydride, sodium borohydride, sodium cyanoborohydride, tin chloride, and the like. In some embodiments, the reducing agent is a borohydride reducing agent. In some embodiments, the reducing agent is sodium borohydride.

In some embodiments, the reaction of the compound of Formula (6) with a reducing agent is performed in the presence of a solvent. In some embodiments, organic solvents include, without limitation, dimethylformamide, dimethylsulfoxide, 1,4-dioxane, N-methylpyrrolidone, tetrahydrofuran, 2-methyl-tetrahydrofuran, toluene, and the like. In some embodiments, the solvent comprises toluene. In some embodiments, the solvent comprises THF. In some embodiments, the organic solvent is any compatible mixture of organic solvents such as those given as embodiments herein, such as a mixture of toluene and THF. In some embodiments, the reaction is performed at a temperature of between about −15° C. and about −5° C. It is to be understood that any combination of the foregoing conditions is contemplated, for instance, the reaction of a reducing agent with the compound of Formula (6) may be performed in the presence of toluene, tetrahydrofuran, or toluene and tetrahydrofuran. For instance, the reaction of a reducing agent with the compound of Formula (6) may be performed in the presence of toluene, tetrahydrofuran, or toluene and tetrahydrofuran, at a temperature of between about −15° C. and about −5° C. In some such embodiments, the reducing agent is sodium borohydride.

In some embodiments, the compound of Formula (5) is isolated as a solid. In some embodiments, the compound of Formula (5) is isolated by precipitation or recrystallization. In some embodiments, the compound of Formula (5) is isolated from a mixture of ethyl acetate and n-heptane.

Preparation of the Compound of Formula (6)

In some embodiments, the compound of Formula (6) is prepared by reacting (R)-tert-butanesulfinamide with a compound of Formula (7):

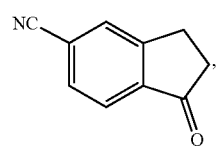

to form the compound of Formula (6) or a salt thereof. In some embodiments, the reaction is performed in the presence of a Lewis acid and a water scavenger. In some embodiments, reagents that act as both a Lewis acid and a water scavenger include, without limitation, CuSO$_4$, GaCl$_3$, Ti(OEt)$_4$, and the like. In some embodiments, the reaction is performed in the presence of Ti(OEt)$_4$. In some embodiments, the reaction is performed in toluene. In some embodiments, the reaction is performed at a temperature of between about 75° C. and about 85° C. In some embodiments, the compound of formula (6) is used without work-up. In some embodiments, the compound of formula (6) is used without purification. In some embodiments, the compound of formula (6) is not isolated. In some embodiments, the compound of formula (6) is formed in situ. It is to be understood that any combination of the foregoing conditions is contemplated, for instance, reacting (R)-tert-butanesulfinamide with a compound of Formula (7) may be performed in the presence of Ti(OEt)$_4$ in toluene. For instance, reacting (R)-tert-butanesulfinamide with a compound of Formula (7) may be performed in the presence of Ti(OEt)$_4$ in toluene at a temperature of between about 75° C. and about 85° C.

Preparation of the Compound of Formula (7)

In some embodiments, the compound of formula (7) is prepared by converting a compound of Formula (8)

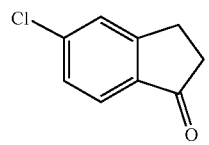

(8)

to the compound of Formula (7). In some embodiments, conversion of the compound of Formula (8) to the compound of Formula (7) comprises reacting the compound of Formula (8) via a palladium-catalyzed cyanation reaction with a cyanation reagent. In some embodiments, cyanation reagents include, without limitation, KCN, NaCN, Zn(CN)$_2$, CuCN, trimethylsilylcyanide, and ferricyanide. In some embodiments, the reaction comprises reacting the compound of Formula (8) with Zn(CN)$_2$ in the presence of a palladium catalyst. In some embodiments, the reaction comprises reacting the compound of Formula (8) with Zn(CN)$_2$ in the presence of XPhos and Pd$_2$(dba)$_3$. In some embodiments, the reaction is performed at a temperature of between about 85° C. and about 95° C.

In some embodiments, the compound of Formula (7) is purified by hot filtration and/or recrystallization. In some embodiments, the compound of Formula (7) is purified by hot filtration in ethanol. In some embodiments, the compound of Formula (7) is purified by hot filtration at a temperature of greater than about 60° C. In some embodiments, the compound of Formula (7) is purified by hot filtration at a temperature of about 70° C., about 75° C., about 78° C., or about 80° C. In some embodiments, the compound of Formula (7) is purified by recrystallization. In some embodiments, the solvent for recrystallization comprises ethanol. In some embodiments, the solvent for recrystallization comprises water. In some embodiments, the solvent for recrystallization comprises a mixture of ethanol and water. In some embodiments, the recrystallization is performed at a temperature of between about 0° C. and about 78° C. In some embodiments, the recrystallization is performed at a temperature of between about 0° C. and about 70° C. In some embodiments, the recrystallization is performed at a temperature of between about 0° C. and about 60° C. In some embodiments, the recrystallization is started at a temperature of between about 50° C. and about 60° C., followed by cooling to a temperature of between about 0° C. and about 10° C.

It is to be understood that any combination of the foregoing conditions is contemplated, for instance, in some embodiments the reaction comprises reacting the compound of Formula (8) with XPhos, Pd$_2$(dba)$_3$, and Zn(CN)$_2$ in the presence of DMF and 2-MeTHF. For instance, in some embodiments the reaction comprises reacting the compound of Formula (8) with XPhos, Pd$_2$(dba)$_3$, and Zn(CN)$_2$ in the presence of DMF and 2-MeTHF at a temperature of between about 85° C. and about 95° C., followed by hot filtration in ethanol, followed by recrystallization in a mixture of ethanol and water.

Scheme 3 illustrates a scheme of synthesizing the HCl salt of the compound of Formula (4).

Scheme 3

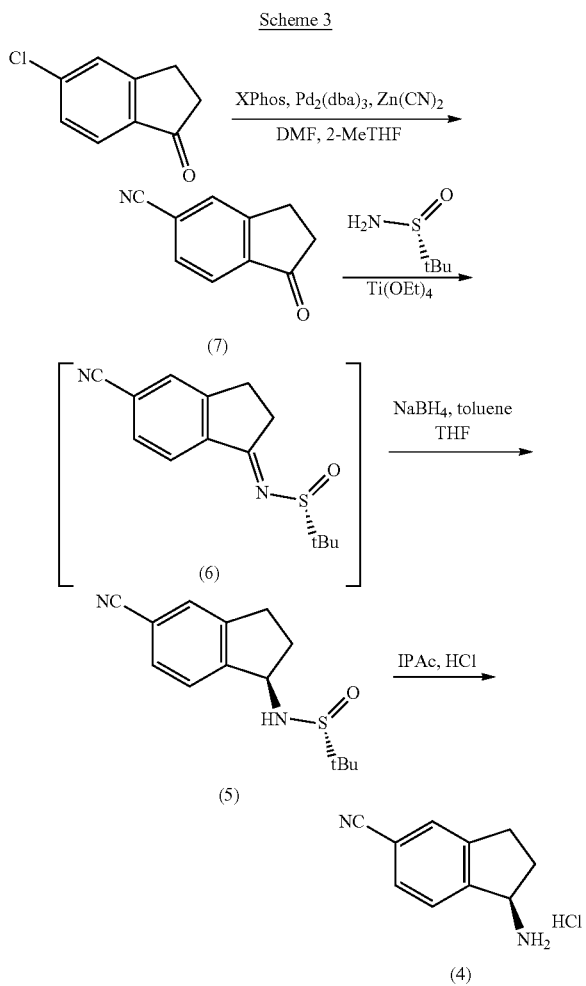

The foregoing methods of preparing the compound of Formula (4), which is (R)-1-amino-2,3-dihydro-1H-indene-5-carbonitrile, or a salt thereof (e.g. (R)-1-amino-2,3-dihydro-1H-indene-5-carbonitrile hydrochloride), demonstrate improvements over previous synthetic methods in the art. For instance, the methods described herein require fewer synthetic steps, avoid the isolation and/or purification of certain intermediates, require fewer isolated intermediates, and afford greater overall yield relative to the methods provided in U.S. Publication No. US2006/0173183A1 and WO 2006/083454, which describes the preparation of (R)-1-amino-2,3-dihydro-1H-indene-5-carbonitrile hydrochloride from 5-bromo-indan-1-ylamine. For instance, the methods described herein require fewer synthetic steps and afford greater overall yield and eliminate the need for protecting groups, in addition to eliminating the need for tin or azide reagents, relative to the methods provided in U.S. Pat. No. 10,836,755, which describe the preparation of tert-butyl (R)-(5-cyano-2,3-dihydro-1H-inden-1-yl)carbamate from 5-bromo-2,3-dihydro-1H-inden-1-one.

Alternate Preparation of a Compound of Formula (4)

In another aspect, provided herein is a method of preparing a compound of Formula (4):

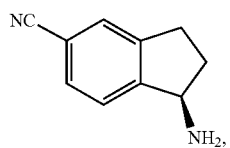

(4)

or a salt thereof, by converting a compound of Formula (A)

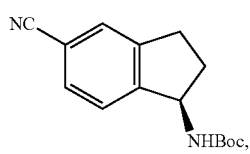

(A)

or a salt thereof, to the compound of Formula (4) or a salt thereof. In some embodiments, the method comprises converting a compound of Formula (A) to the compound of Formula (4) or a salt thereof. In some embodiments, conversion of the compound of Formula (A) to the compound of Formula (4) comprises reacting the compound of Formula (A) with an acid. In some embodiments, the acid is an inorganic acid. In some embodiments, inorganic acids include, without limitation, hydrochloric acid, hydrobromic acid, sulfuric acid, nitric acid, phosphoric acid, and the like. In some embodiments, the aqueous acid is an organic acid. In some embodiments, organic acids include acetic acid, propionic acid, ascorbic acid, citric acid, trifluoroacetic acid, toluenesulfonic acid, and the like. In some embodiments, the acid is toluenesulfonic acid. In some embodiments, the acid is trifluoroacetic acid. In some embodiments, the compound of Formula (4) or salt thereof is isolated by vacuum filtration. In some embodiments, the compound of Formula (4) or salt thereof is purified by washing the solids with an organic solvent. In some embodiments, the compound of Formula (4) or salt thereof is purified by washing the solids with petroleum ether.

In some embodiments, the compound of Formula (A) or a salt thereof is prepared by converting a compound of Formula (B)

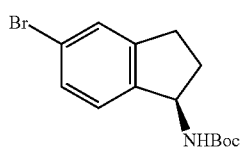

(B)

or a salt thereof, to the compound of Formula (A). In some embodiments, the method comprises converting a compound of Formula (B) to a compound of Formula (A). In some embodiments, conversion of the compound of Formula (B) or salt thereof to the compound of Formula (A) or salt thereof comprises reacting the compound of Formula (B) or salt thereof via a palladium-catalyzed cyanation reaction. In some embodiments, the reaction comprises reacting the compound of Formula (B) or salt thereof with potassium ferricyanide in the presence of a palladium catalyst. In some embodiments, the reaction comprises reacting the compound of Formula (B) or salt thereof with potassium ferricyanide in the presence of XPhos Pd G2 and/or XPhos. In some embodiments, the reaction is performed in the presence of a base. In some embodiments, the base is an acetate base. In some embodiments, the base is potassium acetate.

In some embodiments, the compound of Formula (A) is purified by trituration in ethyl acetate hexanes. In some embodiments, the compound of Formula (A) is purified by trituration in 10% by volume ethyl acetate in hexanes. In some embodiments, the compound of Formula (A) is purified by column chromatography. In some embodiments, the column chromatography comprises a silica gel column. In some embodiments, the compound of Formula (A) is eluted from the column with ethyl acetate in petroleum ether. In some embodiments, the compound of Formula (D) is eluted from the column with 15% by volume ethyl acetate in petroleum ether.

In some embodiments, the compound of Formula (B) or a salt thereof is prepared by converting a compound of Formula (C)

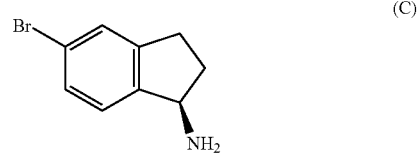 [SMILES: N[C@@H]1CCc2cc(Br)ccc21]

(C)

or a salt thereof, to the compound of Formula (B) or a salt thereof. In some embodiments, the method comprises converting a compound of Formula (C) or salt thereof to a compound of Formula (B). In some embodiments, the compound of Formula (B) is prepared by reacting the compound of Formula (C) or salt thereof with di-tert-butyl dicarbonate. In some embodiments, conversion of the compound of Formula (C) to the compound of Formula (B) further comprises reacting the compound of Formula (C) with di-tert-butyl dicarbonate in the presence of a base. In some embodiments, bases include, without limitation, N,N-diisopropylethylamine, trimethylamine, diethylamine, triethylamine, tributylamine, collidine, lutidine, pyridine, picoline, dicyclohexylamine, morpholine, DBU, DBN, imidazole, benzimidazole, histidine, guanidine, and the like. In some embodiments, the base is triethylamine. In some embodiments, the compound of Formula (B) is purified by trituration in hexanes.

In some embodiments, the compound of Formula (C) or a salt thereof is prepared by converting a compound of Formula (D)

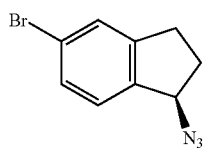

(D)

to the compound of Formula (C) or a salt thereof. In some embodiments, the method comprises converting a compound of Formula (D) to a compound of Formula (C). In some embodiments, conversion of the compound of Formula (D) to the compound of Formula (C) or salt thereof comprises reacting the compound of Formula (D) with a reducing agent. In some embodiments, reducing agents include, without limitation, triphenylphosphine, zinc, sodium borohydride, tin chloride, lithium aluminum hydride, sodium borohydride, hydrogen in the presence of a catalyst such as a palladium catalyst, and the like. In some embodiments, the reducing agent is tin chloride. In some embodiments, the compound of Formula (C) is used without purification. In some embodiments, the compound of Formula (C) is purified by acid-base extraction.

In some embodiments, the compound of Formula (D) or a salt thereof is prepared by converting a compound of Formula (E)

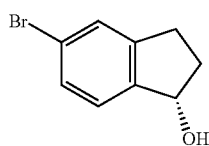

(E)

or salt thereof to the compound of Formula (D). In some embodiments, the method comprises converting a compound of Formula (E) to the compound of Formula (D). In some embodiments, conversion of the compound of formula (E) or salt thereof to the compound of Formula (D) comprises reacting the compound of formula (E) or salt thereof with an azide reagent. In some embodiments, azide reagents include, without limitation, sodium azide, diphenylphosphoryl azide, trimethylsilyl azide, hydrazoic acid, and the like. In some embodiments, the reaction of the compound of formula (E) or salt thereof with an azide reagent further comprises a base. In some embodiments, the base is DBU. In some embodiments, the compound of Formula (D) is purified by column chromatography. In some embodiments, the column chromatography comprises a silica gel column packed with 1% triethylamine in petroleum ether. In some embodiments, the compound of Formula (D) is eluted from the column with petroleum ether.

In some embodiments, the compound of Formula (E) or a salt thereof is prepared by converting a compound of Formula (F)

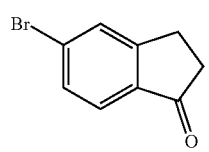

(F)

to the compound of Formula (E) or a salt thereof. In some embodiments, conversion of the compound of Formula (F) to the compound of Formula (E) or salt thereof comprises subjecting the compound of Formula (F) to reducing conditions to form the compound of Formula (E). In some embodiments, the reducing conditions comprise a reducing agent. In some embodiments, reducing agents include, without limitation, hydrogen in the presence of a catalyst such as a palladium catalyst, lithium aluminum hydride, sodium borohydride, sodium cyanoborohydride, borane, and the like. In some embodiments, the reducing conditions comprise a reducing agent and a chiral reagent. In some embodiments, chiral reagents include, without limitation, chiral oxazaborolidines such as (3R)-1-methyl-3,3-diphenyl-hexahydropyrrolo[1,2-c][1,3,2]oxazaborole (Corey-Bakshi-Shibata catalyst), (S)-3,3-diphenyltetrahydro-1H,3H-pyrrolo[1,2-c][1,3,2]oxazaborole, (S)-1-butyl-3,3-diphenyltetrahydro-1H,3H-pyrrolo[1,2-c][1,3,2]oxazaborol, and the like. In some embodiments, the reducing conditions comprise borane. In some embodiments, the reducing conditions comprise (3R)-1-methyl-3,3-diphenyl-hexahydropyrrolo[1,2-c][1,3,2]oxazaborole and borane. In some embodiments, the reducing conditions comprise (3R)-1-methyl-3,3-bis(3,5-dimethylphenyl)-hexahydropyrrolo[1,2-c][1,3,2]oxazaborole and borane. In some embodiments, the compound of Formula (E) is purified by column chromatography. In some embodiments, the column chromatography comprises a silica gel column packed with 1% triethylamine in petroleum ether. In some embodiments, the compound of Formula (D) is eluted from the column with ethyl acetate in petroleum ether. In some embodiments, the compound of Formula (D) is eluted from the column with 30% by volume ethyl acetate in petroleum ether. In some embodiments, the compound of Formula (D) is further purified by trituration in hexane.

Scheme 4 illustrates an alternative scheme of synthesizing the HCl salt of the compound of Formula (4).

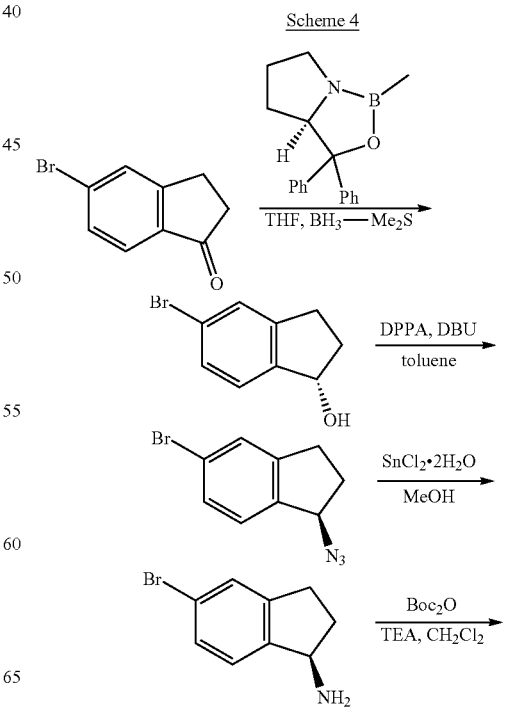

Scheme 4

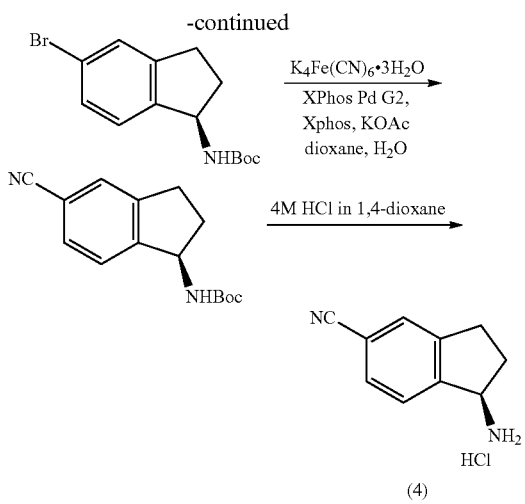

In another aspect, provided herein is a method of preparing a compound of Formula (4):

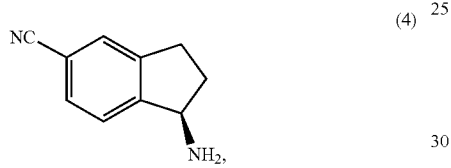

or salt thereof, by isolating the compound of Formula (4) ((R)-1-amino-2,3-dihydro-1H-indene-5-carbonitrile or salt thereof) by chiral purification of 1-amino-2,3-dihydro-1H-indene-5-carbonitrile or a salt thereof. In some embodiments, 1-amino-2,3-dihydro-1H-indene-5-carbonitrile or salt thereof is prepared by reductive amination of the compound of Formula (F) by methods known in the art.

In some embodiments, the method of preparing the compound of Formula (1) or a salt thereof further comprises obtaining the compound of Formula (4) or a salt thereof by any of the methods described herein.

Chromatography, recrystallization and other conventional separation procedures may also be used with intermediates or final products where it is desired to obtain a particular isomer of a compound or to otherwise purify a product of a reaction.

Certain processes provided herein are described in reference to the illustrative synthetic schemes shown below and the specific examples that follow. Certain reactions and conversions described herein can be conducted using methods known in the art. For example, U.S. Pat. No. 10,836,755 describe methods and reagents that can be used to synthesize certain compounds disclosed herein. Skilled artisans will recognize that, to obtain various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. In addition, one of skill in the art will recognize that protecting groups may be used to protect certain functional groups (amino, carboxy, or side chain groups) from reaction conditions, and that such groups are removed under standard conditions when appropriate.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

EXAMPLES

Abbreviations used herein are explained in the following table.

| Abbreviation | Meaning |
| --- | --- |
| ACN | Acetonitrile |
| Aq. | Aqueous |
| CDI | Carbonyldiimidazole |
| DBU | 1,8-Diazabicyclo[5.4.0]undec-7-ene |
| DCM | Dichloromethane |
| DMF | N,N-Dimethylformamide |
| EtOAc | Ethyl acetate |
| EtOH | Ethanol |
| HPLC | High performance liquid chromatography |
| IPAc | Isopropyl acetate |
| LOD | Limit of detection |
| IPC | In-process control |
| NMP | N-Methylpyrrolidone |
| THF | Tetrahydrofuran |
| 2-MeTHF | 2-Methyl tetrahydrofuran |

Example 1. Synthesis of 1-oxo-2,3-dihydro-1H-indene-5-carbonitrile

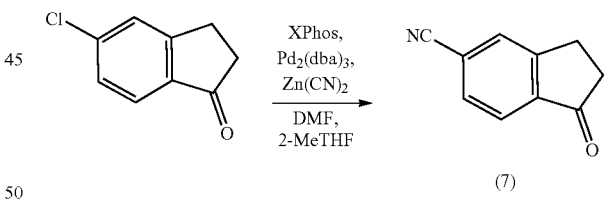

5-Chloro-1-indanone (70.0 kg, 420.17 mol, 1.00 equiv.) was dissolved in a mixture of dimethylformamide (DMF, 280 kg, 296.6 L) and 2-methyl tetrahydrofuran (2-MeTHF, 280 kg, 327.9 L) and thoroughly degassed. XPhos (2.2 kg, 4.61 mol, 0.011 equiv.) and Pd$_2$(dba)$_3$ (2.1 kg, 2.29 mol, 0.0055 equiv.) were then added to the reaction solution and the mixture was heated to 85-95° C. In a separate flask, 2-MeTHF (140 kg, 163.9 L) was added to zinc cyanide (Zn(CN)$_2$, 27.3 kg, 232.5 mol, 0.55 equiv.); the heterogeneous mixture was degassed and this slurry was added to the hot reaction mixture above. Agitation at 85-95° C. was continued until the in-process control (IPC) with an acceptance limit of ≤5% area of 5-chloro-1-indanone was met. The mixture is subsequently cooled to 20-30° C. and dichloromethane (DCM, 500 kg, 375.9 L) was added to the reaction mixture.

In a separate vessel, potassium carbonate (116.9 kg, 845.9 mol, 2.0 equiv.) and water (630 kg, 630 L) were agitated at 20-30° C. to give a homogeneous solution, which was then added to the crude reaction mixture above. The quenched reaction mixture was filtered through a Celite pad (20.3 kg) and washed with DCM (690 kg, 518.8 L). The layers of the biphasic filtrate were separated and the upper aqueous layer was extracted with an additional portion of DCM (210 kg, 157.9 L). The combined lower organic phases were washed with water (350 kg, 350 L) and filtered through a silica gel pad (21 kg) and washed with DCM (140 kg, 105.3 L). The reaction mixture was concentrated and a solvent swap to ethanol (EtOH, 2×70 kg, 2×88.7 L) was performed and the solution was concentrated to dryness. Ethanol (700 kg, 887.2 L) was added to the residue and the mixture was heated to 70-80° C., hot filtered and cooled to 60° C. The filtrate was concentrated under vacuum at <60° C. to a afford a solid. Ethanol (180 kg, 228.1 L) was added to the crude product and the mixture was warmed to 50-60° C. to affect dissolution. Water (28 kg, 28 L) is added and the reaction mixture was subsequently cooled to 0-10° C. The recrystallized product was isolated by filtration and dried at <60° C. to give 1-oxo-2,3-dihydro-1H-indene-5-carbonitrile as a yellow solid in 70.2% yield.

Example 2. Synthesis of (R)—N—((R)-5-cyano-2,3-dihydro-M-inden-1-yl)-2-methylpropane-2-sulfinamide

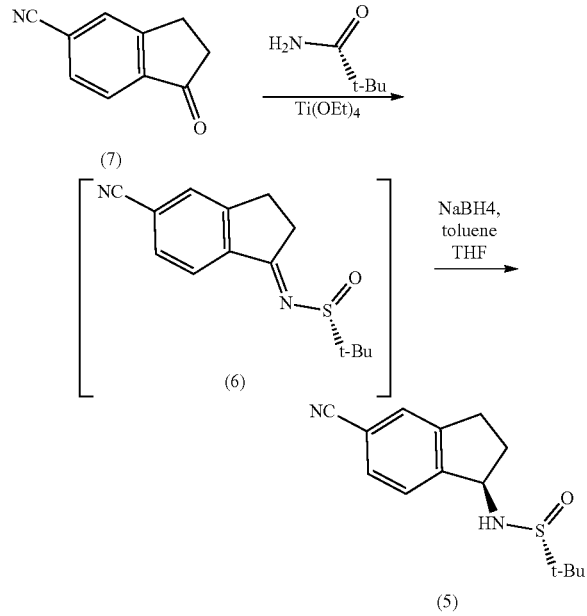

(R)-tert-butanesulfinamide (66.7 kg, 550.3 mol, 2.22 equiv.) and titanium ethoxide (Ti(OEt)$_4$, 113.3 kg, 496.7 mol, 2.00 equiv.) were stirred in toluene (135.3 kg, 156.1 L) and the mixture was warmed to 75-85° C. over 3 hours. A solution of 1-oxo-2,3-dihydro-1H-indene-5-carbonitrile (39.0 kg, 248.1 mol, 1.00 equiv.) in toluene (286 kg) was then added to the reaction mixture while maintaining the temperature at 75-85° C. The mixture was agitated at this temperature for 3-4 hours. The preparation of intermediate (R)—N-(5-cyano-2,3-dihydro-1H-inden-1-ylidene)-2-methylpropane-2-sulfinamide was considered complete when IPC-1 with an acceptance limit of ≤0.5% residual 1-oxo-2,3-dihydro-1H-indene-5-carbonitrile was met.

The reaction mixture was cooled to 20-30° C. and THF (172.8 kg, 194.4 L) was added followed by portion-wise addition of sodium borohydride (NaBH$_4$, 4.7 kg, 124.2 mol, 0.5 equiv.) keeping the temperature of the reaction mixture between −15 and −10° C. The reaction mixture was stirred at a temperature of −10 to −5° C. for 14-20 hours until IPC-2 with a specification limit of residual (R)—N-(5-cyano-2,3-dihydro-1H-inden-1-ylidene)-2-methylpropane-2-sulfinamide ≤2% was met.

The reaction mixture was warmed to 20-30° C. and added to a 2.5M solution of potassium glycolate (483.8 kg). The reactor was rinsed with toluene (182.1 kg, 210.0 L) and the wash was added to the quenching solution. The thick slurry was stirred for 20-40 min and then the layers were allowed to separate over 1-3 h. The lower aqueous layer was separated and the solids were retained with the organic layer. The organic layer was washed twice with 2.5M potassium glycolate (2×132.6 kg) and twice with 10% sodium chloride (2×124.8 kg). The organic layer was then filtered through pad of Celite (4.6 kg) and washed with toluene (2×39 kg, 2×45 L).

The combined toluene layers were concentrated to dryness and a solvent swap with ethyl acetate (EtOAc, 2×117 kg, 2×129.7 L) was performed and the solution was concentrated to dryness. The residue was dissolved into EtOAc (117 kg, 129.7 L) at 60-70° C. and the solution was stirred at this temperature for 1 hour before n-heptane (234 kg, 242.1 L) was added slowly, maintaining the temperature at 60-70° C. for 1-2 hours. The reaction mixture was cooled to 0-5° C. over a period of 4-5 hours and agitated for an additional 2-3 hours at this temperature. The solids were isolated by centrifugation and the cake was washed with a cooled (0-5° C.) solution of EtOAc (26 kg, 28.8 L) and n-heptane (51.8 kg, 75.7 L). The crude product was dried at 20-30° C. for 8-10 hours to give 42.2 kg (64.8%) of (R)—N—((R)-5-cyano-2,3-dihydro-1H-inden-1-yl)-2-methylpropane-2-sulfinamide.

Example 3: Synthesis of (R)-1-amino-2,3-dihydro-M-indene-5-carbonitrile hydrochloride

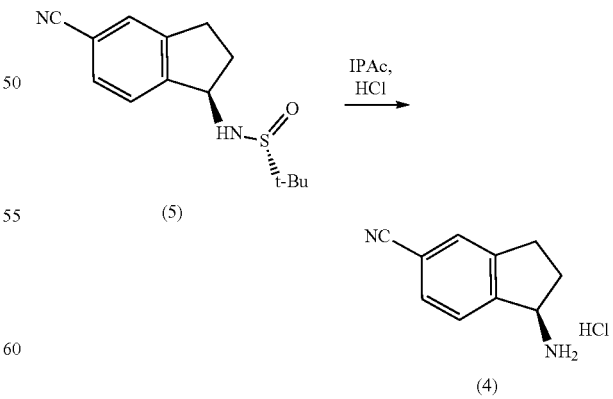

Isopropyl acetate (IPAc, 942 kg, 1082.8 L) was added to (R)—N—((R)-5-cyano-2,3-dihydro-1H-inden-1-yl)-2-methylpropane-2-sulfinamide (42.2 kg, 160.8 mol, 1.00 equiv.) and the solution was treated with 6M HCl (39 kg, 197.7 mol, 1.23 equiv.) for a period of 16-20 hours until IPC-3 was satisfied; residual (R)—N—((R)-5-cyano-2,3-dihydro-1H-inden-1-yl)-2-methylpropane-2-sulfinamide ≤0.5%. Crude (R)-1-amino-2,3-dihydro-1H-indene-5-carbonitrile hydrochloride was isolated by centrifuge. The wet cake was washed with IPAc (130 kg 149.4 L) and dried at 30-40° C. for 16-24 hours and the LOD was measured (report, result: 0.28% w/w). The (R)-1-amino-2,3-dihydro-1H-indene-5-carbonitrile hydrochloride product was analyzed for purity (specification: ≥98.0% area, result: 99.7% area), chiral purity (specification: ≥99.0%, result: 99.7% area) and Karl Fischer titration (report, result: 0.45% w/w). The title compound was isolated in 91.1% yield.

Example 4: Synthesis of (S)-5-bromo-2,3-dihydro-1H-inden-1-ol

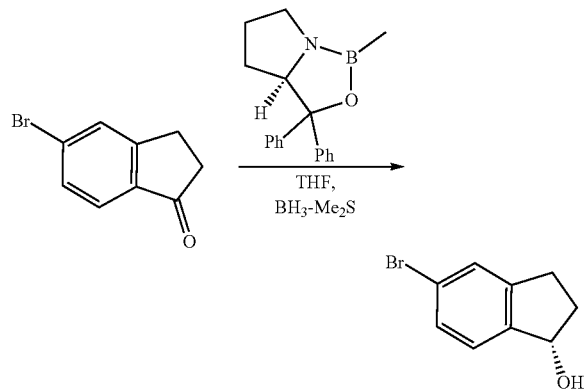

To a solution of 5-bromo-2,3-dihydro-1H-inden-1-one (50 g, 237 mmol, 1.0 equiv) in THF (400 mL) under a nitrogen atmosphere was added (3R)-1-methyl-3,3-diphenyl-hexahydropyrrolo[1,2-c][1,3,2]oxazaborole (37 mL of 1 M in toluene, 0.15 equiv). The mixture was cooled to −10° C. and borane dimethyl sulfide (10 M in THF) (32.2 g, 1.4 equiv) was added dropwise with stirring over 1 h. After stirring for 3 h at −10° C., the reaction was quenched by slow addition of water (200 mL). The resulting solution was extracted with ethyl acetate (200 mL) three times. The combined organic layers were washed with brine (300 mL), dried over anhydrous sodium sulfate, and concentrated. The residue was purified using a silica gel column packed with 1% TEA in petroleum ether (30% ethyl acetate/petroleum ether) to give a solid that was triturated with hexane (300 mL) to afford 38.0 g (75%) of (1S)-5-bromo-2,3-dihydro-1H-inden-1-ol as a light yellow solid. LRMS (ES): calculated for $C_9H_9BrO$, 212.0 Da, measured 195 m/z [M+H−18]$^+$.

Example 5: Synthesis of (R)-1-azido-5-bromo-2,3-dihydro-1H-indene

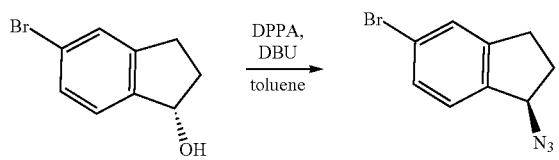 [SMILES: O[C@H]1CCc2cc(Br)ccc21 ; [N-]=[N+]=N[C@@H]1CCc2cc(Br)ccc21]

To a solution of (S)-5-bromo-2,3-dihydro-1H-inden-1-ol (42 g, 197 mmol, 1.0 equiv) in toluene (500 mL) was added diphenylphosphorylazide (74.3 g, 270.0 mmol, 1.4 equiv) under nitrogen. To this mixture was added DBU (45 g, 295 mmol, 1.5 equiv) dropwise with stirring at 0° C. over 1 h. After stirring for 3 h between 0 to 15° C., the mixture was diluted with ethyl acetate (400 mL) and washed with water (400 mL) three times. The organic layer was dried over anhydrous sodium sulfate, concentrated, and purified using a silica gel column packed with 1% TEA in petroleum ether (eluted with petroleum ether) to give 44.4 g (95%) of (R)-1-azido-5-bromo-2,3-dihydro-1H-indene as dark brown oil. The dark brown oil was used in next step without further purification. LRMS (ES): calculated for $C_9H_8BrN_3$, 237.0 Da, measured 195, 197 m/z [M+H−42]$^+$.

Example 6: Synthesis of (R)-5-bromo-2,3-dihydro-M-inden-1-amine

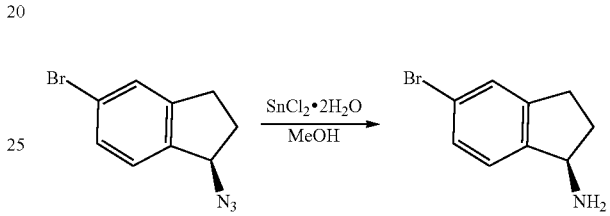

To a solution of (R)-1-azido-5-bromo-2,3-dihydro-1H-indene (44.3 g, 186 mmol, 1.0 equiv) in methanol (600 mL) was slowly added SnCl$_2$·2H$_2$O (76 g, 337 mmol, 1.81 equiv). After stirring overnight at rt, the mixture was diluted with ethyl acetate (500 mL) and NaOH (2 N, 700 mL), stirred at rt for 1 h, and filtered. The filtrate was separated and the aqueous layer was extracted with ethyl acetate (300 mL). The combined organic layers were extracted with HCl (1 N, 500 mL) twice and the aqueous layers were combined. The pH of the aqueous layer was adjusted to 11 with saturated sodium hydroxide and extracted with ethyl acetate (300 mL) three times. The combined organic layers were dried over anhydrous sodium sulfate and concentrated to give 31.8 g (80%) of (R)-5-bromo-2,3-dihydro-1H-inden-1-amine as yellow oil. LRMS (ES): calculated for $C_9H_{10}BrN$, 211.0 Da, measured 195, 197 m/z [M+H−16]$^+$.

Example 7: Synthesis of tert-butyl (R)-(5-bromo-2,3-dihydro-M-inden-1-yl)carbamate

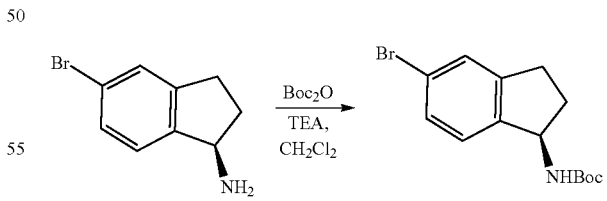

To a solution of (R)-5-bromo-2,3-dihydro-1H-inden-1-amine (31.8 g, 150 mmol, 1.0 equiv) in CH$_2$Cl$_2$ (500 mL) was added TEA (22.7 g, 224.8 mmol, 1.5 equiv) and a solution of (Boc)$_2$O (39.2 g, 180 mmol, 1.2 equiv) in CH$_2$Cl$_2$ (150 mL) dropwise at −5° C. over a period of 45 min. The mixture was then warmed to rt, stirred for 2 h, diluted with CH$_2$Cl$_2$ (200 mL), washed with water (500 mL) and brine (200 mL) twice, dried over anhydrous sodium sulfate, and concentrated. The solid was triturated with hexanes (300 mL) to give 38.7 g (83%) of tert-butyl (R)-(5-bromo-2,3-dihydro-1H-inden-1-yl)carbamate as a white solid. LRMS (ES): calculated for $C_{14}H_{18}BrNO_2$, 311.1 Da, measured 256, 258 m/z $[M+H-56]^+$.

Example 8: Synthesis of tert-butyl (R)-(5-cyano-2,3-dihydro-M-inden-1-yl)carbamate

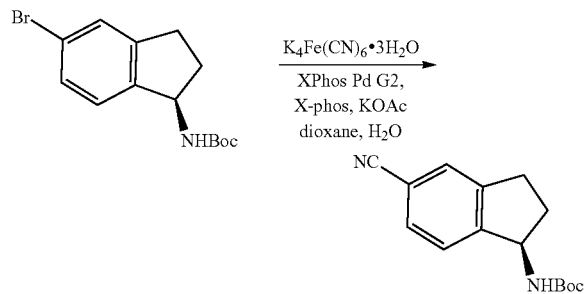

To a solution of tert-butyl (R)-(5-bromo-2,3-dihydro-1H-inden-1-yl)carbamate (25.5 g, 81.7 mmol, 1.00 equiv) in dioxane under a nitrogen atmosphere (270 mL) were added $K_4Fe(CN)_6 \cdot 3H_2O$ (17.3 g, 41 mmol, 0.5 equiv), chloro(2-dicyclohexylphosphino-2',4',6'-triisopropyl-1,1'-biphenyl)[2-(2'-amino-1,1'-biphenyl)]palladium(II) (2nd Generation XPhos precatalyst, 965 mg, 1.2 mmol, 0.02 equiv), X-phos (584 mg, 1.2 mmol, 0.01 equiv), and a solution of KOAc (16.0 g, 163 mmol, 2.0 equiv) in water (270 mL). After stirring at 105° C. for 5 h, the resulting solution was diluted with ethyl acetate (500 mL). The solids were removed by filtration. The filtrate was separated and the aqueous layer was extracted with ethyl acetate (300 mL) twice. The combined organic layers were washed with brine (300 mL), dried over anhydrous sodium sulfate, and concentrated, and purified using silica gel chromatography (15% ethyl acetate/petroleum ether) to give 20.0 g (94%) of tert-butyl (R)-(5-cyano-2,3-dihydro-1H-inden-1-yl)carbamate. LRMS (ES): calculated for $C_{15}H_{18}N_2O_2$, 258.1 Da, measured 259 m/z $[M+H]^+$.

Example 9: Synthesis of (R)-1-amino-2,3-dihydro-M-indene-5-carbonitrile hydrochloride

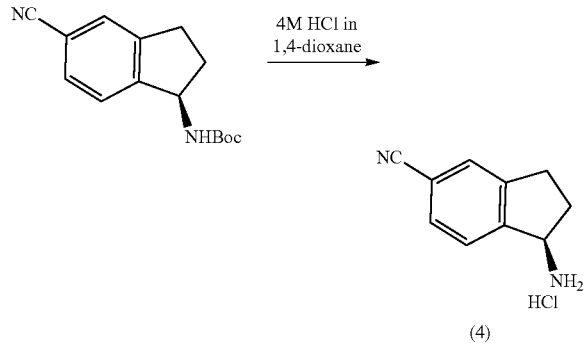

To a solution of tert-butyl (R)-(5-cyano-2,3-dihydro-1H-inden-1-yl)carbamate (20.0 g, 77 mmol, 1.0 equiv) in $CH_2Cl_2$ was added 4 M HCl in dioxane (192.5 mL, 770 mmol, 10 equiv). The mixture was stirred overnight and diluted with ethyl acetate (500 mL). The precipitated solids were collected by filtration, washed with petroleum ether (200 mL) twice, and dried to afford (R)-1-amino-2,3-dihydro-1H-indene-5-carbonitrile hydrochloride (13.0 g, 86%) as a white solid. LRMS (ES): calculated for $C_{10}H_{10}O_2$, 158.1 Da, measured 159 m/z $[M+H]^+$.

Example 10: Synthesis of (R)—N-(5-cyano-2,3-dihydro-1H-inden-1-yl)-1-methyl-1H-pyrazole-4-carboxamide

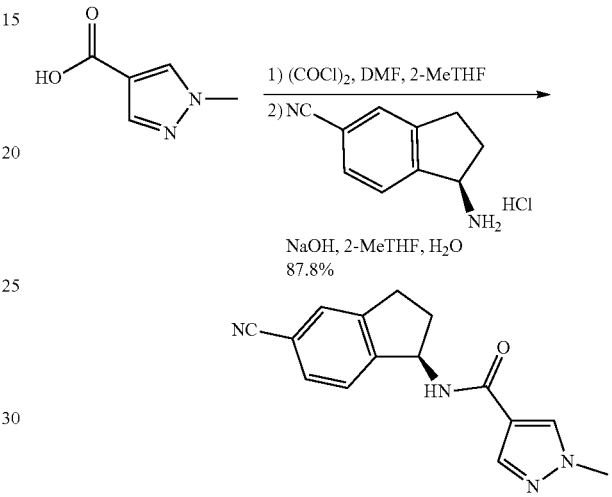

A reactor was charged with 1-methyl-1H-pyrazole-4-carboxylic acid (12.2 kg, 96.73 mol, 1.00 equiv.), 2-MeTHF (76.9 kg, 89.4 L), and DMF (62.9 g, 66.6 mL, 0.861 mol, 0.0089 equiv.). Oxalyl chloride (11.7 kg, 91.89 mol, 0.95 equiv.) was slowly added over the period of at least 45 minutes while maintaining a temperature below 35° C. The transfer line was rinsed with 2-MeTHF (6.1 kg) and the rinse was sent to the reactor. The resulting mixture was agitated at 30±5° C. After agitation at 30±5° C. for at least 8 hours (actual reaction time: 19.3 h), an IPC sample was pulled and analyzed via HPLC. The reaction was considered to be complete when the IPC was met (specification: 1-methyl-1H-pyrazole-4-carboxylic acid ≤15% area; result 9.6% 1-methyl-1H-pyrazole-4-carboxylic acid). The reaction mixture is used directly for the synthesis of (R)—N-(5-cyano-2,3-dihydro-1H-inden-1-yl)-1-methyl-1H-pyrazole-4-carboxamide without work up.

Solid NaOH (14.6 kg, 366.0 mol, 3.78 equiv.) was dissolved in 78.3 kg of water.

A separate reactor was charged with (R)-1-amino-2,3-dihydro-1H-indene-5-carbonitrile hydrochloride (17.9 kg, 91.89 mol, 0.95 equiv.) and 2-MeTHF (63.9 kg, 74.3 L). The prepared 4N NaOH solution (92.9 kg) was added to the mixture while maintaining a temperature <30° C. The drum containing NaOH solution as rinsed with water (12.2 kg) and the rinse was transferred to the reaction vessel. The mixture was stirred at 20° C. for 30 min and a clear two-phase solution was obtained. The prepared 1-methyl-1H-pyrazole-4-carboxylic acid and acid chloride solution in 2-MeTHF was transferred to the free amine solution slowly over a period of at least 20 min while maintaining an internal temperature of <30° C. The reactor used for acid chloride was rinsed with 2-MeTHF (12.2 kg, 14.2 L) and the rinse was added to the reaction mixture. A lot of solid formed after addition of the acid chloride. The resulting mixture was agitated at 20±5° C. for at least 5 hours (actual reaction time: 17.8 h) and the reaction was considered to be complete when the IPC was met (specification: (R)-1-amino-2,3-dihydro-1H-indene-5-carbonitrile was ≤5%; result 0.7%).

The solid product, (R)—N-(5-cyano-2,3-dihydro-1H-inden-1-yl)-1-methyl-1H-pyrazole-4-carboxamide, was collected by filtration and the wet cake was washed with 2-MeTHF (24.4 kg, 28.4 L), water (3×211.5 kg, 1×36.6 kg). The pH of filtrate after the last water wash was tested (specification: pH 8.5±1.5; result pH 8.7).

The material was dried in a tray dryer under vacuum <45° C. with a slow nitrogen bleed for at least 20 h until the LOD was met (specification: ≤3% w/w; result: 0.8% w/w). The product is dried for 64.7 hours to afford 21.5 kg (87.8% yield) of (R)—N-(5-cyano-2,3-dihydro-1H-inden-1-yl)-1-methyl-1H-pyrazole-4-carboxamide, which is analyzed for purity (specification: ≥97.0% area, result: 99.4% area).

Example 11: Synthesis of (R)—N-(5-(N'-hydroxycarbamimidoyl)-2,3-dihydro-1H-inden-1-yl)-1-methyl-1H-pyrazole-4-carboxamide

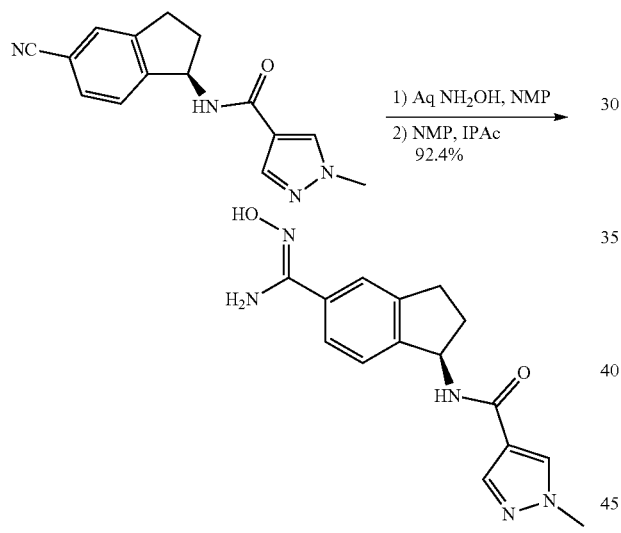

An NMP (108.2 kg, 105.3 L, 5.0 vol) solution of (R)—N-(5-cyano-2,3-dihydro-1H-inden-1-yl)-1-methyl-1H-pyrazole-4-carboxamide (21.0 kg, 78.86 mol, 1.00 equiv.) was cooled to 5±5° C. and 50% aqueous hydroxylamine (15.6 kg, 236.58 mol, 3.00 equiv.) was slowly added over a period of at least 10 min while maintaining an internal temperature of ≤10° C. The mixture was slowly warmed up to 20±5° C. over a period of at least 2 h and agitated at 20±5° C. for at least 16 h (actual reaction time: 19.7 h). An IPC was taken for reaction completion (specification: ≤2% CK-3834025 result: 0.05% CK-3834025, 0.65% by-product amide).

After the reaction was complete, the mixture is heated to 65±5° C. (a clear solution). IPAc (182.8 kg, 209.6 L, 10.0 vol) was slowly charged over the period of at least 1 hour while maintaining an internal temperature ≥50° C. A lot of solid formed after addition of IPAc. The resulting mixture was stirred at 60±5° C. for 1 h. The mixture was slowly cooled to 20±5° C. over a period of 4 h and stirred at 20±5° C. for at least 8 hours (actual period: stirred for 15.3 h). The solid was collected via filtration. The wet cake was washed with IPAc [2×98.8 kg (2×113.3 L, 2×5.4 vol)]. The material was initially dried on the filter through pulling vacuum for at least 1 h. A sample of (R)—N-(5-(N'-hydroxycarbamimidoyl)-2,3-dihydro-1H-inden-1-yl)-1-methyl-1H-pyrazole-4-carboxamide wet cake was pulled and analyzed via HPLC. Result: 99.49% product (R)—N-(5-(N'-hydroxycarbamimidoyl)-2,3-dihydro-1H-inden-1-yl)-1-methyl-1H-pyrazole-4-carboxamide, 0.27% by-product amide. Starting material (R)—N-(5-cyano-2,3-dihydro-1H-inden-1-yl)-1-methyl-1H-pyrazole-4-carboxamide was not detected. The material was dried in a vacuum tray dryer at ≤50° C. for at least 24 h (actual drying time: 24.3 h) until the LOD specification was met (specification: LOD ≤1% w/w; result: 0.10% w/w).

(R)—N-(5-(N'-hydroxycarbamimidoyl)-2,3-dihydro-1H-inden-1-yl)-1-methyl-1H-pyrazole-4-carboxamide was analyzed for purity (specification: ≥95% area; result: 99.5% area (R)—N-(5-(N'-hydroxycarbamimidoyl)-2,3-dihydro-1H-inden-1-yl)-1-methyl-1H-pyrazole-4-carboxamide, 0.26% area by-product amide). A total of 21.8 kg of (R)—N-(5-(N'-hydroxycarbamimidoyl)-2,3-dihydro-1H-inden-1-yl)-1-methyl-1H-pyrazole-4-carboxamide (92.4% yield) was obtained.

Example 12: Synthesis of (R)—N-(5-(5-ethyl-1,2,4-oxadiazol-3-yl)-2,3-dihydro-1H-inden-1-yl)-1-methyl-1H-pyrazole-4-carboxamide

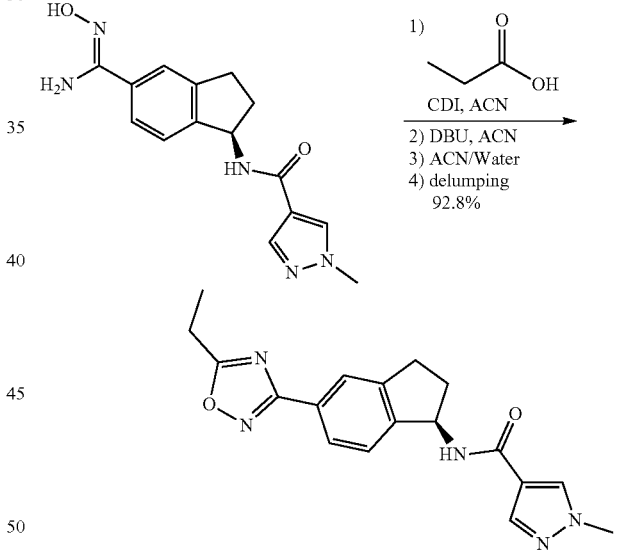

A reactor (vessel 1) was charged with CDI (11.9 kg, 73.67 mol, 1.05 equiv.) and CH$_3$CN (131.4 kg, 167.2 L) and the resulting mixture was treated with propionic acid (5.7 kg, 77.18 mol, 1.10 equiv.) maintaining a temperature of <25° C. The transfer line was rinsed with CH$_3$CN (10.2 kg, 13.0 L) and the rinse was transferred the bulk reaction mixture. The resulting clear solution was stirred at 20±5° C. for at least 1 h. The reaction was considered to be complete when the IPC was met (specification: free propionic acid ≤20 mol % by $^1$H NMR; result: 4.8% free propionic acid).

A separate reactor (vessel 2) was charged with (R)—N-(5-(N'-hydroxycarbamimidoyl)-2,3-dihydro-1H-inden-1-yl)-1-methyl-1H-pyrazole-4-carboxamide (21.0 kg, 70.16 mol, 1.00 equiv.) and CH$_3$CN (40.4 kg, 51.4 L). The freshly prepared active imidazole solution in vessel 1 was transferred to vessel 2. Vessel 1 was rinsed with CH$_3$CN (20.2 kg, 25.7 L) and the rinse was transferred to added to vessel 2. The mixture was heated to 50±5° C. The reaction was stirred at this temperature for at least 12 hours (actual reaction time: 16.6 hours). The mixture was a slurry that as easily stirred. An IPC sample was taken (specification: (R)—N-(5-(N'-hydroxycarbamimidoyl)-2,3-dihydro-1H-inden-1-yl)-1-methyl-1H-pyrazole-4-carboxamide ≤2%, result: 0.28%).

The reaction was then charged with DBU (21.4 kg, 140.32 mol, 2.00 equiv.). The transfer line was rinsed with CH$_3$CN (6.5 kg, 8.3 L) and the rinse was transferred to the bulk solution. The temperature was adjusted to 70±5° C. and the mixture as stirred at 70±5° C. for at least 2 h until the IPC was met (specification: imidazole intermediate ≤2 area %; result: 0.16% imidazole intermediate).

The reaction mixture was quenched with the addition of water (64.6 kg) while maintaining the temperature ≥50° C. The temperature was adjusted to 55±5° C. and polish filtered. The solution was concentrated at a temperature of ≤50° C. but not below 10° C. until the batch volume was ~200 L. The thick slurry was heated to 75±5° C. and the clear solution was diluted with water (417.3 kg) while maintaining the temperature ≥70° C. The temperature was adjusted to 75±5° C. and the mixture was stirred at 75±5° C. for 2 h. Then the mixture was then slowly cooled to 20±5° C. over a period of at least 4 h. The mixture was stirred 20±5° C. for at least 2 h (actual reaction time: 11.5 h).

The solid was collected by filtration and the wet cake was washed with water (3×161.5 kg). The solid was dried in a vacuum oven at ≤50° C. with a slow nitrogen bleed for at least 24 h (actual drying time: 48 h) and analyzed for LOD (specification: LOD ≤1% w/w; result: LOD 0.05% w/w).

The dried (R)—N-(5-(5-ethyl-1,2,4-oxadiazol-3-yl)-2,3-dihydro-1H-inden-1-yl)-1-methyl-1H-pyrazole-4-carboxamide was analyzed for purity (specification: ≥97% area; result: 100% area). A total of 22.0 kg of (R)—N-(5-(5-ethyl-1,2,4-oxadiazol-3-yl)-2,3-dihydro-1H-inden-1-yl)-1-methyl-1H-pyrazole-4-carboxamide (92.8% yield) was obtained. The product (22.0 kg) was then de-lumped to give 21.4 kg (97.3%).

Example 13: Synthesis of (R)—N-(5-cyano-2,3-dihydro-1H-inden-1-yl)-1-methyl-1H-pyrazole-4-carboxamide

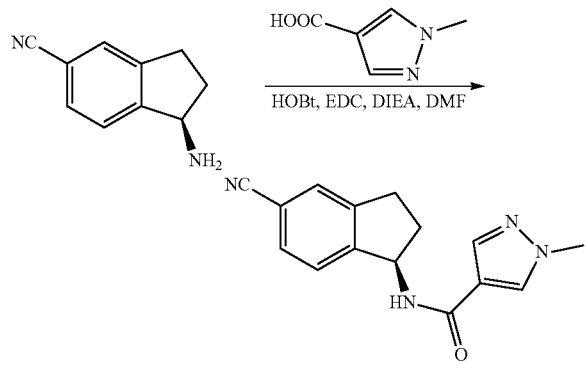

To a mixture of 1-methyl-1H-pyrazole-4-carboxylic acid (2.3 g, 18.2 mmol, 1.2 equiv), HOBt (2.1 g, 15.1 mmol, 1.0 equiv), and EDC (5.8 g, 30.3 mmol, 2.0 equiv) in DMF (10 mL) was added DIEA (7.5 mL, 45.4 mmol, 3.0 equiv). The mixture was stirred for 10 min, followed by addition of (R)-1-amino-2,3-dihydro-1H-indene-5-carbonitrile hydrochloride (2.9 g, 15.1 mmol, 1.0 equiv). The reaction mixture was stirred overnight and then diluted with water (60 mL). The solid was collected, washed with water (20 mL), and dried to give 3.5 g (86%) of (R)—N-(5-cyano-2,3-dihydro-1H-inden-1-yl)-1-methyl-1H-pyrazole-4-carboxamide as an off-white solid. $^1$H NMR (400 MHz, methylene chloride-d$_2$) δ 7.86 (s, 1H), 7.74 (d, J=0.8 Hz, 1H), 7.60-7.48 (m, 2H), 7.48-7.42 (m, 1H), 6.06 (d, J=8.4 Hz, 1H), 5.69 (q, J=8.3 Hz, 1H), 3.94 (s, 3H), 3.15-2.90 (m, 2H), 2.74-2.64 (m, 1H), 2.03-1.90 (m, 1H). LRMS (ES): calculated for C$_{15}$H$_{14}$NO, 266.1 Da, measured 267.1 m/z [M+H]$^+$.

Example 14: (R)—N-(5-(N'-hydroxycarbamimidoyl)-2,3-dihydro-1H-inden-1-yl)-1-methyl-1H-pyrazole-4-carboxamide

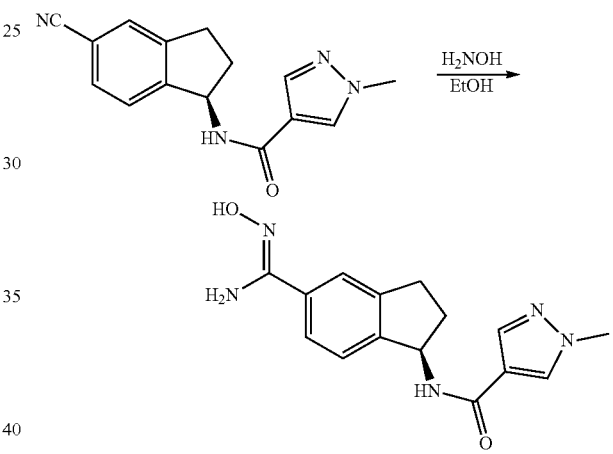

To a suspension of (R)—N-(5-cyano-2,3-dihydro-1H-inden-1-yl)-1-methyl-1H-pyrazole-4-carboxamide (3.0 g, 11.3 mmol, 1.0 equiv) in EtOH (20 mL) was added hydroxylamine (50% w/w in water, 4.0 mL). The mixture was heated to 80° C. for 3 h and concentrated to afford 3.3 g (98%) of (R,Z)—N-(5-(N'-hydroxycarbamimidoyl)-2,3-dihydro-1H-inden-1-yl)-1-methyl-1H-pyrazole-4-carboxamide as an off-white solid. LRMS (ES): calculated for C$_{15}$H$_{17}$N$_5$O$_2$, 299.1 Da, measured 300.1 m/z [M+H]$^+$.

Example 15: (R)—N-(5-(N'-hydroxycarbamimidoyl)-2,3-dihydro-1H-inden-1-yl)-1-methyl-1H-pyrazole-4-carboxamide

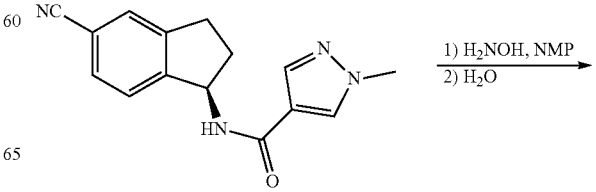

-continued

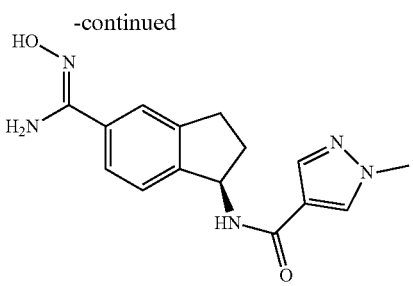

To a solution of (R)—N-(5-cyano-2,3-dihydro-1H-inden-1-yl)-1-methyl-1H-pyrazole-4-carboxamide (24.0 g, 89.5 mmol, 1.0 equiv.) in NMP (120 mL) was added hydroxylamine (50% w/w in water, 17.7 g, 3.0 equiv.). The mixture was stirred at rt for 18 hours and water (240 mL) was added, The reaction mixture gave a thin slurry, which was filtered and washed with DI water (120 mL×3) over 2 hours to afford 25.1 g (93.1%) of (R)—N-(5-(N'-hydroxycarbamimidoyl)-2,3-dihydro-1H-inden-1-yl)-1-methyl-1H-pyrazole-4-carboxamide as an off-white solid. LRMS (ES): calculated for $C_{15}H_{17}N_5O_2$, 299.1 Da, measured 300.1 m/z $[M+H]^+$.

The invention claimed is:

1. A method of preparing a compound of Formula (1):

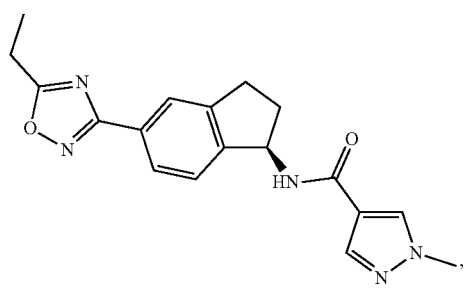

(1)

or a salt thereof, comprising:
(i) converting a compound of Formula (7)

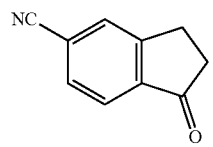

(7)

to a compound of Formula (6)

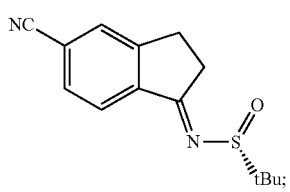

(6)

(ii) converting the compound of Formula (6) to a compound of Formula (5)

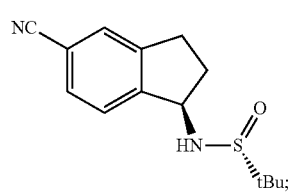

(5)

and
(iii) converting the compound of Formula (5) to the compound of Formula (1) or salt thereof.

2. The method of claim 1, wherein converting the compound of Formula (7) to the compound of Formula (6) comprises reacting the compound of Formula (7) with (R)-tert-butanesulfinamide.

3. The method of claim 2, wherein reacting the compound of Formula (7) with (R)-tert-butanesulfinamide is performed in the presence of a Lewis acid.

4. The method of claim 2, wherein reacting the compound of Formula (7) with (R)-tert-butanesulfinamide is performed in the presence of a water scavenger.

5. The method of claim 2, wherein reacting the compound of Formula (7) with (R)-tert-butanesulfinamide is performed in the presence of titanium ethoxide.

6. The method of claim 2, wherein reacting the compound of Formula (7) with (R)-tert-butanesulfinamide is performed in the presence of toluene at a temperature of between about 75° C. and about 85° C.

7. The method of claim 1, wherein converting the compound of Formula (6) to the compound of Formula (5) comprises reacting the compound of Formula (6) with a reducing agent.

8. The method of claim 7, wherein reacting the compound of Formula (6) with a reducing agent is performed in the presence of tetrahydrofuran at a temperature of between about −15° C. and about −5° C.

9. The method of claim 7, wherein the reducing agent is sodium borohydride.

10. The method of claim 1, wherein the compound of Formula (6) is used without work-up or purification.

11. The method of claim 1, wherein converting the compound of Formula (5) to the compound of Formula (1) or salt thereof comprises converting the compound of Formula (5) to a compound of Formula (4)

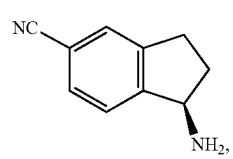

(4)

or a salt thereof.

12. The method of claim 11, wherein converting the compound of Formula (5) to the compound of Formula (4) or salt thereof comprises hydrolyzing the sulfinamide of the compound of Formula (5).

13. The method of claim 12, wherein hydrolyzing the sulfinamide of the compound of Formula (5) is performed in the presence of an aqueous acid.

14. The method of claim 11, wherein the compound of Formula (4) is prepared as a hydrochloride salt.

15. The method of claim 11, wherein the compound of Formula (4) is prepared as a 4-methylbenzenesulfonate salt.

16. The method of claim 11, further comprising obtaining the compound of Formula (4) by reacting the salt of the compound of Formula (4) with a base.

17. The method of claim 11, wherein converting the compound of Formula (5) to the compound of Formula (1) or salt thereof further comprises converting the compound of Formula (4) or salt thereof to a compound of Formula (3)

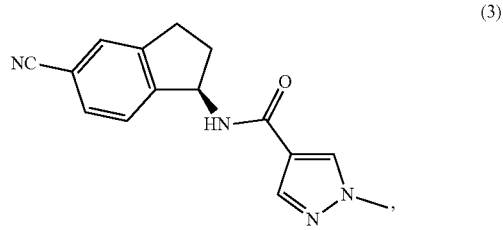 [SMILES: Cn1cc(C(=O)N[C@@H]2CCc3cc(C#N)ccc32)cn1]

or a salt thereof.

18. The method of claim 17, wherein converting the compound of Formula (4) or salt thereof to the compound of Formula (3) or salt thereof comprises:
    (i) reacting 1-methyl-1H-pyrazole-4-carboxylic acid with a carboxylic acid activating agent to form an activated 1-methyl-1H-pyrazole-4-carboxylic acid, and
    (ii) reacting the activated 1-methyl-1H-pyrazole-4-carboxylic acid with the compound of Formula (4) or salt thereof, to form the compound of Formula (3) or salt thereof.

19. The method of claim 18, wherein the carboxylic acid activating agent is oxalyl chloride.

20. The method of claim 18, wherein the carboxylic acid activating agent comprises a carbodiimide reagent.

21. The method of claim 18, wherein the carboxylic acid activating agent comprises a carbodiimide reagent and hydroxybenzotriazole.

22. The method of claim 17, wherein converting the compound of Formula (5) to the compound of Formula (1) or salt thereof further comprises converting the compound of Formula (3) or salt thereof to a compound of Formula (2)

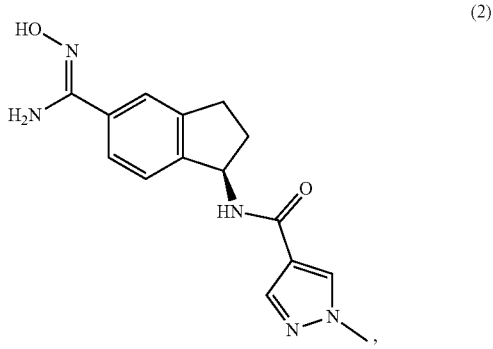 [SMILES: Cn1cc(C(=O)N[C@@H]2CCc3cc(/C(N)=N/O)ccc32)cn1]

or a salt thereof.

23. The method of claim 22, wherein converting the compound of Formula (3) or salt thereof to the compound of Formula (2) or salt thereof comprises reacting hydroxylamine with the compound of Formula (3) or salt thereof.

24. The method of claim 23, wherein reacting the compound of Formula (3) or salt thereof with hydroxylamine is performed at a temperature of 25° C. or lower.

25. The method of claim 23, wherein reacting the compound of Formula (3) or salt thereof with hydroxylamine is performed in the presence of N-methylpyrrolidone.

26. The method of claim 22, wherein converting the compound of Formula (5) to the compound of Formula (1) or salt thereof further comprises converting the compound of Formula (2) or salt thereof to the compound of Formula (1) or salt thereof.

27. The method of claim 26, wherein converting the compound of Formula (2) or salt thereof to the compound of Formula (1) or salt thereof comprises:
    (i) reacting propionic acid with a second carboxylic acid activating agent to form an activated propionic acid, and
    (ii) reacting the activated propionic acid with the compound of Formula (2) or salt thereof.

28. The method of claim 27, wherein the second carboxylic acid activating agent is carbonyldiimidazole.

29. A method of preparing a compound of Formula (4)

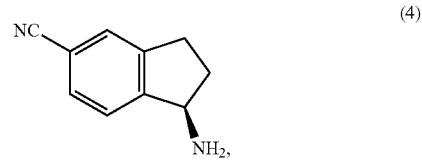 [SMILES: N#Cc1ccc2c(c1)CC[C@H]2N]

or a salt thereof, comprising converting a compound of Formula (5):

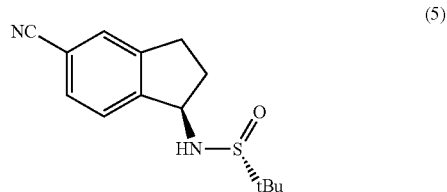 [SMILES: CC(C)(C)[S@@](=O)N[C@@H]1CCc2cc(C#N)ccc21]

to the compound of Formula (4) or salt thereof.

30. The method of claim 29, further comprising obtaining the compound of Formula (5) by reacting a reducing agent with a compound of Formula (6):

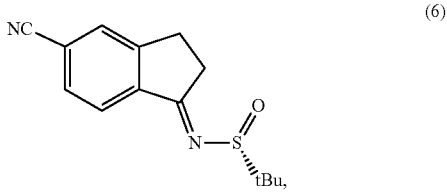 [SMILES: CC(C)(C)[S@@](=O)/N=C1\CCc2cc(C#N)ccc21]

to form the compound of Formula (5).

31. The method of claim 30, wherein the reducing agent is a borohydride reducing agent.

32. The method of claim 30, further comprising obtaining the compound of Formula (6) by reacting (R)-tert-butanesulfinamide with a compound of Formula (7):

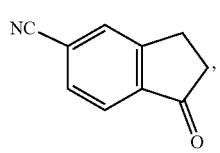
(7)
to form the compound of Formula (6).
* * * * *